United States Patent [19]
Zhang

[11] Patent Number: 6,037,500
[45] Date of Patent: Mar. 14, 2000

[54] ASYMMETRIC SYNTHESIS CATALYZED BY TRANSITION METAL COMPLEXES WITH CYCLIC CHIRAL PHOSPHINE LIGANDS

[75] Inventor: Xumu Zhang, State College, Pa.

[73] Assignee: The Penn State Research Foundation, University Park, Pa.

[21] Appl. No.: 08/876,120

[22] Filed: Jun. 13, 1997

Related U.S. Application Data

[60] Provisional application No. 60/019,938, Jun. 14, 1996, provisional application No. 60/033,493, Dec. 20, 1996, and provisional application No. 60/046,121, May 9, 1997.

[51] Int. Cl.$^7$ .................................................... C07F 9/02
[52] U.S. Cl. ................................. 568/12; 568/13; 568/17
[58] Field of Search ................................. 568/12, 13, 15, 568/17

[56] References Cited

U.S. PATENT DOCUMENTS

| | | |
|---|---|---|
| 3,105,096 | 9/1963 | Welcher et al. . |
| 3,400,163 | 9/1968 | Mason et al. . |
| 5,008,457 | 4/1991 | Burk . |
| 5,171,892 | 12/1992 | Burk . |
| 5,177,230 | 1/1993 | Burk . |
| 5,258,553 | 11/1993 | Burk . |
| 5,426,223 | 6/1995 | Burk . |
| 5,596,114 | 1/1997 | Burk . |

FOREIGN PATENT DOCUMENTS

| | | |
|---|---|---|
| WO 95/05354 | 2/1995 | WIPO . |
| WO 95/06025 | 3/1995 | WIPO . |
| WO 97/13763 | 4/1997 | WIPO . |

OTHER PUBLICATIONS

CA:126:211870 ab of J Am Chem Soc by Zhu 119(7), pp. 1799–1800, 1997.
CA:127:5076 ab of J Org Chem by Chen, 62(13), pp. 4521–4523, Jun. 1997.
CA:113:212107 ab of J of Heterocyclic Chem by Sutton, 27(4) pp. 1123–1126, 1990.
CA:118:255118 ab of US5171892, Dec. 1992.
CA:123:313386 ab of WO9505354, Feb. 1995.
CA:80:1462999 ab of NL7312880, Nov. 1973.
Halterman et al., (1987), *J. Am. Chem. Soc.*, 109: 8105–8107.
Fruyzuk et al., (Sep. 1977), *J. Am. Chem. Soc.*, 99:19, pp. 6262–6267.
Kagan et al., (Sep. 1972), *Asymmetric Catalytic Reduction*, 94:18, pp. 6429–6433.
Achiwa, (Dec. 1976), *J. Amer. Chem Soc.*, 98:25, pp. 8265–8266.
MacNeil, et al., (1981), *J. Am. Chem. Soc.*, 103: 2273–2280.
Takaya et al., (1980), *J. Am. Chem. Soc.*, 102:7932–7934.
Corey et al., (1976), *J. Org. Chem.*, vol. 41, No. 2, pp. 260–265.
Greidinger et al., (Nov. 1957), *Alicycilc Studies*, vol. 22, pp. 1406–1410.
Brown et al., (1982), *J. Org. Chem.*, vol. 47, pp. 5074–5083.
Takaya et al., (1986), *J. Org. Chem.*, vol. 51, pp. 629–635.
Miyashita et al., (1984), *Tetrahedron*, vol. 40, No. 8, pp. 1245–1253.
Burk, Mark, (1991), *J. Am. Chem. Soc.*, vol. 113, pp. 8518–8519.
Vineyard et al., (Aug. 1977), *J. Am. Chem. Soc.*, vol. 99:18, 5946–5952.
Ojima et al., (1980), *Tethrahedron Letters*, vol. 21, pp. 1051–1054.
Burk et al., (1990), *Organometallics*, 9: pp. 2653–2655.
Nagel et al., (1986), *Chem. Ber.*, 119: 3326–3343.
Knowles et al., (1972), *J.C.S. Chem. Comm.*, pp. 10–11.
Chen et al., (1991), *Organometallics*, 10: 3449–3458.
Trost et al., (1996), *Chem. Rev.*, 96: 395–422.
Consiglio et al., (1989), *Chem. Rev.*, 89: 257–276.
Takaya et al., *Organic Syntheis*, pp. 57–63.
Brunner et al., (Sep. 1988), *Synthesis*, pp. 645–654.
Minami et al., (1990), *Tetrahedron Letters*, vol. 31, No. 27, pp. 3905–3908.
Chen et al., (1997), *J. Org. Chem.*, 62: 4521–4523.
Hamada, Y. et al., "New Monodentate Chiral Phosphine 2,6–Dimethyl–9–phenyl–9–phosphabicyclo(3.3.1)nonane (9–PBN): Application to Asymmetric Allylic Substitution Reaction," *Tetrahedron Letters*, Vol. 37, No. 42, pp. 7565–7568 (1996).

*Primary Examiner*—Gary Geist
*Assistant Examiner*—Jean F Vollano
*Attorney, Agent, or Firm*—Finnegan, Henderson, Farabow, Garrett & Dunner, L.L.P.

[57] ABSTRACT

The present invention relates to rigid chiral ligands usefull in making catalysts for asymmetric synthesis. More particularly, the present invention relates to new monodentate and bidentate cyclic chiral phosphine ligands which are formed into catalysts to provide high selectivity of the enantiomeric structure of the end-product.

29 Claims, 15 Drawing Sheets

TYPE 1 BIDENTATE CYCLIC PHOSPHINES

R = ARYL, ALKYL, SUBSTITUTED ARYL OR ALKYL

EXAMPLES 1
 2
 3

4
 5
 6

7
 8
 9

10
 11
 12

13

X = O, NR, S, $CR_2$, C=O, ETC.

TYPE II

X = O, NR, S, CR2, C=O, ETC.

EXAMPLES

TYPE III

TYPE IV

X = O, or NR
SPIRO PHOSPHINES

TYPE V BIDENTATE CYCLIC PHOSPHINES

BRIDGE = ALKYL (E.G., -(CH2)n-, n=2, 3, 4) ARYL BENZENE, FERROCENE, ETC.)

EXAMPLES

TYPE V MONODENTATE CHIRAL PHOSPHINES

EXAMPLES

R1 = ARYL OR ALKYL GROUPS OR SUBSTITUTED ARYL OR ALKYL GROUPS 32    33

X = CHIRAL OXAZOLINES. COOH, OMe, OH, SMe, SH, NR'2, PPH2

34

TYPE VI BIDENTATE CYCLIC PHOSPHINES n = 1,2

EXAMPLES

35

36

37

38

39

R' = CH₃, Et, i-Pr, Ph, ETC.

TYPE VI MONODENTATE CYCLIC PHOSPHINES n = 1,2

R',R = ARYL OR ALKYL GROUPS (e.g., CH₃, Et, i-Pr, Ph, etc.) AND
SUBSTITUTED ARYL AND ALKYL GROUPS X = CHIRAL OXAZOLINES,
COOH, OMe, OH, SMe,
SH, NR'₂, PPh₂

$R_1$, $R_2$, $R_3$, $R_4$ = ARYL OR
ALKYL GROUPS

TYPE VII BIDENTATE CYCLIC PHOSPHINES

EXAMPLES

SYNTHESIS OF TYPE I BIDENTATE CYCLIC PHOSPHINES

SYNTHESIS OF BIDENTATE CYCLIC PHOSPHINES

SYNTHESIS OF MONODENTATE CHIRAL PHOSPHINES

R1 = ARYL OR ALKYL GROUPS

SYNTHESIS OF BIDENTATE CYCLIC PHOSPHINES
n = 1.2

SYNTHESIS OF BIDENTATE CYCLIC PHOSPHINES

R' = Me, Et, PhCH₂, ETC.
X = Br, I, OTs, or OMs

R = Me, Et, i-Pr, Ph

ASYMMETRIC SYNTHESIS CATALYZED BY TRANSITION METAL COMPLEXES WITH CYCLIC CHIRAL PHOSPHINE LIGANDS

This application claims priority to the following U.S. provisional applications: 60/019,938 filed on Jun. 14, 1996; 60/033,493 filed on Dec. 20, 1996; and 60/046,121 filed on May 9, 1997.

TECHNICAL FIELD OF THE INVENTION

The present invention relates to rigid chiral ligands useful in making catalysts for asymmetric synthesis. More particularly, the present invention relates to new monodentate and bidentate cyclic chiral phosphine ligands which are formed into catalysts to provide high selectivity of the enantiomeric structure of the end-product.

BACKGROUND OF THE INVENTION

The biological activities of many pharmaceuticals, fragrances, food additives and agrochemicals are often associated with their absolute molecular configuration. While one enantiomer gives a desired biological function through interactions with natural binding sites, another enantiomer usually does not have the same function and sometimes has deleterious side effects. A growing demand in pharmaceutical industries is to market a chiral drug in enantiomerically pure form. To meet this challenge, chemists have explored many approaches for acquiring enantiomerically pure compounds ranging from optical resolution and structural modification of naturally occurring chiral substances to asymmetric catalysis using synthetic chiral catalysts and enzymes. Among these methods, asymmetric catalysis is often the most efficient because a small amount of a chiral catalyst can be used to produce a large quantity of a chiral target molecule. During the last two decades, great effort has been devoted to discovering new asymmetric catalysts and more than a half-dozen commercial industrial processes have used asymmetric catalysis as the key step in the production of enantiomerically pure compounds.[1]

Asymmetric phosphine ligands have played a significant role in the development of novel transition metal catalyzed asymmetric reactions. Over 1000 chiral diphosphines[2] have been made since the application of the DIPAMP ligand[3] for the industrial production of L-Dopa, yet only a few of these ligands afford the efficiency and selectivity required for commercial applications. Among these ligands, BINAP is one of the most frequently used bidentate chiral phosphines. The axially dissymmetric, fully aromatic BINAP ligand has been demonstrated to be highly effective for many asymmetric reactions. Duphos and related ligands have also shown high enantioselectivities in numerous reactions. However, there are a variety of reactions in which only modest enantioselectivity has been achieved with these ligands. Highly selective chiral ligands are needed to facilitate asymmetric reactions.

FIG. 1 lists known chiral bidentate phosphines (DIPAMT,[3] BPPM,4 DEGPHOS,[5] DIOP,[6] Chiraphos,[7] Skewphos,[8] BINAP,9 Duphos,[10] and BPE[10]). While high selectivities were observed in many reactions using some of these chiral diphosphine ligands, there are many reactions where these ligands are not very efficient in terms of activity and selectivity. There are many disadvantages associated with these ligands, which hinder their applications. For DIPAMP, the phosphine chiral center is difficult to make. This ligand is only useful for asymmetric hydrogenation reaction. For BPPM, DIOP and Skewphos, the methylene group in the ligands causes conformational flexibility and enantioselectivities are moderate for many catalytic asymmetric reaction. DEGPHOS and CHIRAPHOS coordinate transition metal in five-membered ring. The chiral environment created by the phenyl groups is not close to the substrates and enantioselectivities are moderate. BINAP, DuPhos and BPE ligands are good for many asymmetric reactions. However, the rotation of aryl—aryl bond makes BINAP very flexible. The flexibility is an inherent limitation in the use of phosphine ligands. Furthermore, because the BINAP contains three aryl groups, it is less electron donating than phosphines that have less aryl groups. This is an important factor which influences reaction rates. For hydrogenation reactions, electron donating phosphines are more active. For the more electron donating DUPHOS and PBE ligands, the five membered ring adjacent to the phosphines is flexible.

U.S. Pat. Nos. 5,329,015; 5,386,061; 5,532,395 describe phosphines prepared through chiral 1,4-diols. These patents also describe divalent aryl and ferrocene bridging groups. U.S. Pat. No. 5,258,553 describes chiral tridentate ligand phosphine ligands. The above ligands are made into Group VIII transitional catalyst and are used to conduct enantioselective catalytic reactions such as asymmetric hydrogenation of olefins, ketones and imines. These references illustrate the preparation of catalyst from phosphine ligands and the conducting of various asymmetric synthesis. These patent disclosures are incorporated herein by reference.

The present invention discloses several new bidentate and monodentate phosphine ligands for asymmetric catalysis. The common feature of these ligands are that they contain rigid ring structures useful for restricting conformational flexibility of the ligands, thus enhancing chiral recognition. The present invention provides families of chiral diphosphines by variation of the steric and electronic environments (i.e., change of P-M-P bite angles and substituents on phosphine). In such a manner, the present invention provides an efficient and economical method with which to synthesize chiral drugs and agrochemicals.

SUMMARY OF THE INVENTION

Figure 1:
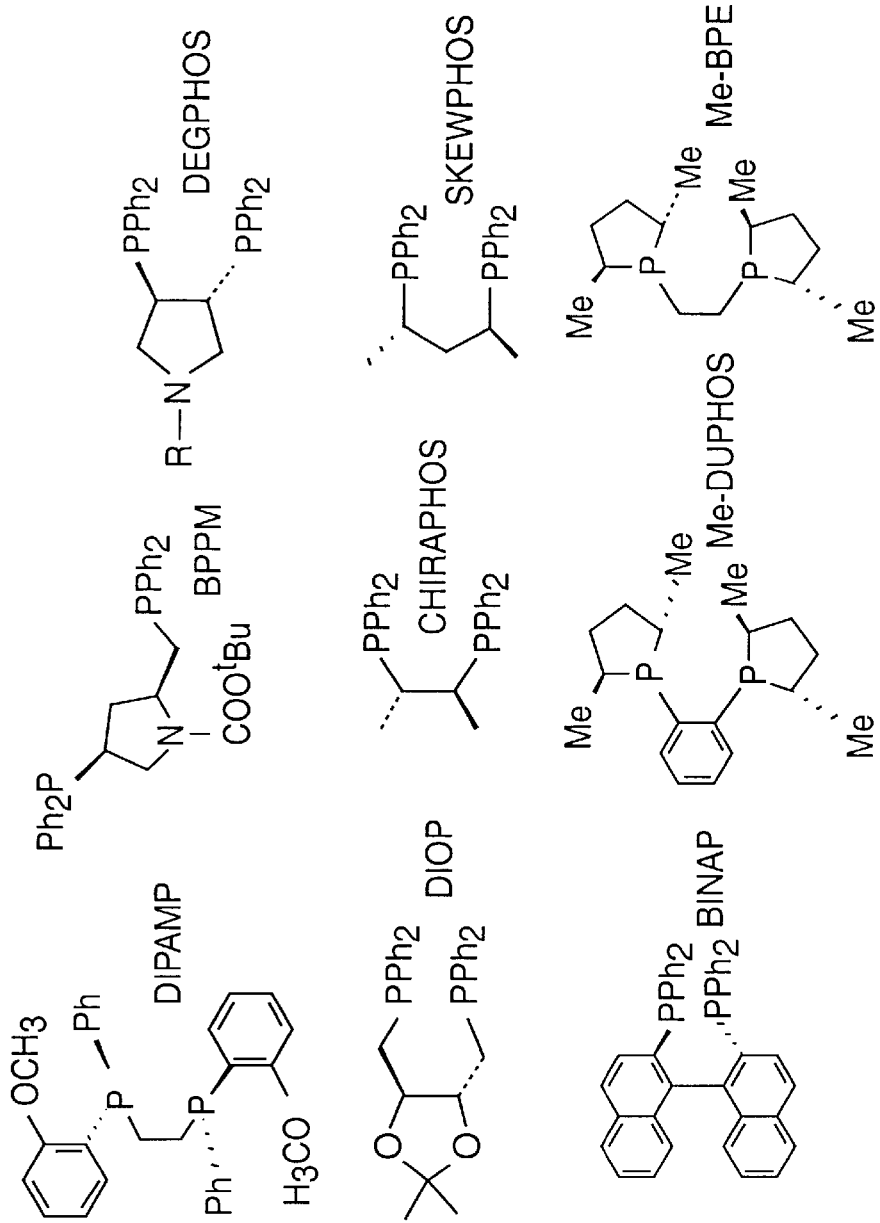
FIG. 1 lists known chiral bidentate phosphines. While high selectivities were obtained in many reactions using some of these chiral diphosphine ligands, there are many reactions where these ligands are not very efficient in terms of activity and selectivity. There are many disadvantages associated with these ligands, which hinder their applications. For DIPAMP, the phosphine chiral center is difficult to make. This ligand is only useful for limited application in asymmetric hydrogenation. For BPPM, DIOP, and Skewphos, the methylene group in the ligands causes conformational flexibility and enantioselectivities are moderate for many catalytic asymmetric reactions. DEGPHOS and CHIRAPHOS coordinate transition metals in five-membered ring. The Chiral environment created by the phenyl groups is not close to the substrates and enantionselectivities are moderate for many reactions. BINAP, DuPhos and BPE ligands are good for many asymmetric reactions. However, the rotation of the aryl—aryl bond makes BINAP very flexible. The flexibility is an inherent limitation in the use of phosphine ligand. Furthermore, because the phosphine of BINAP contains adjacent three aryl groups, it is less electron donating than phosphine that have less aryl groups. This is an important factor which influences reaction rates. For hydrogenation reactions, electron donating phosphines are more active. For the more electron donating DUPHOS and BPE ligands, the five-membered ring adjacent to the phosphines is flexible.
Figure 2:
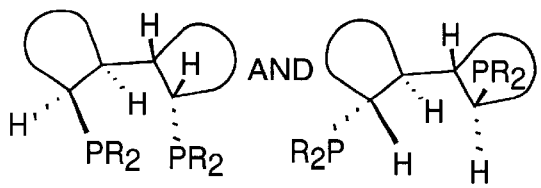
FIG. 2 illustrates ligands 1–13 (Type I). These ligands have at least four chiral centers in their backbones and they can form seven-membered chelating ring with many transition metals. The two cyclic rings in the backbone limit the conformational flexibility. The two carbon stereogenic centers adjacent to $PR_2$ may be inverted as illustrated in FIG. 2.
Figure 2:
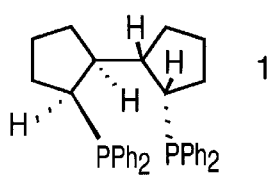
Figure 2:
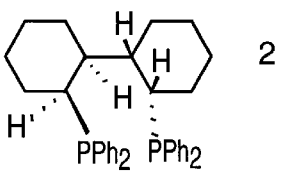
Figure 2:
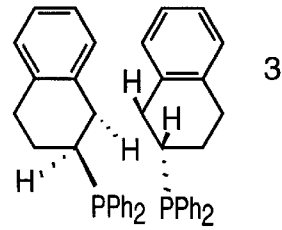
Figure 2:
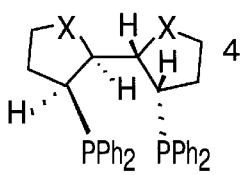
Figure 2:
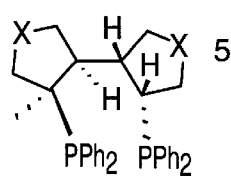
Figure 2:
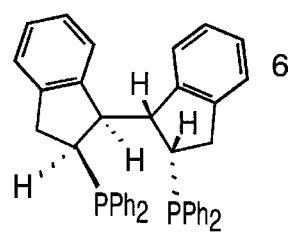
Figure 2:
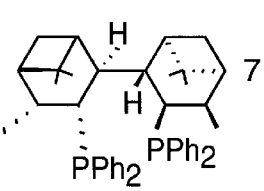
Figure 2:
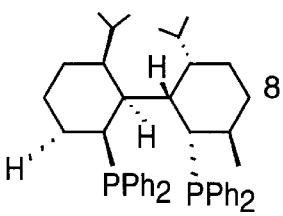
Figure 2:
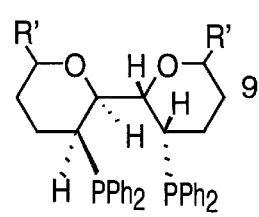
Figure 2:
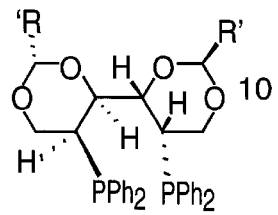
Figure 2:
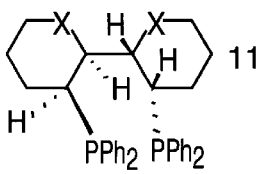
Figure 2:
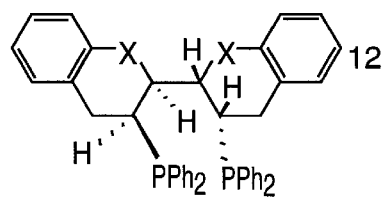
Figure 2:
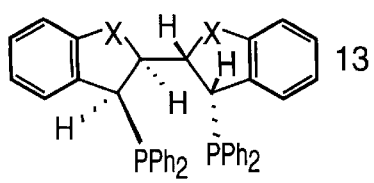
Figure 3:
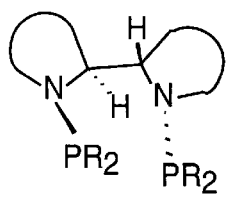
FIG. 3 depicts ligands 14–23. Ligands 14–16 (Type II) have a nitrogen-phosphine bond in the ligands. Ligands 17–19 (Type III) have many phosphine-oxygen bonds. Ligands 20–23 (Type IV) have spiro-ring structure in their backbones. These ligands can be regarded as derivatives of ligands 1–13 with structure variation of their backbones.
Figure 3:
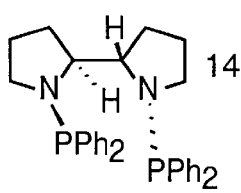
Figure 3:
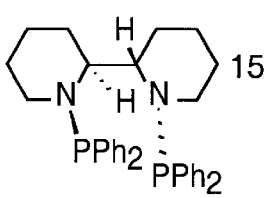
Figure 3:
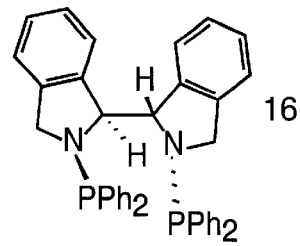
Figure 3:
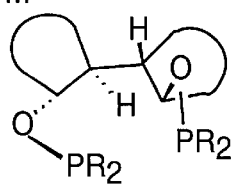
Figure 3:
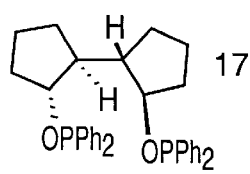
Figure 3:
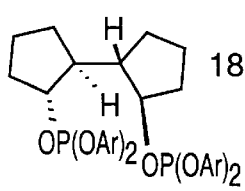
Figure 3:
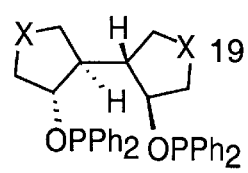
Figure 3:
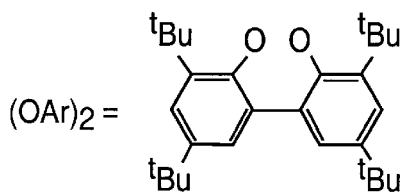
Figure 3:
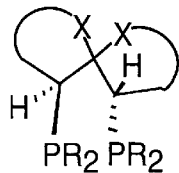
Figure 3:
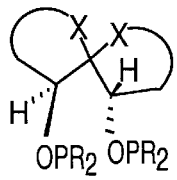
Figure 3:
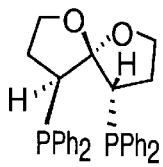
Figure 3:
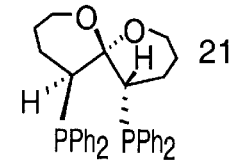
Figure 3:
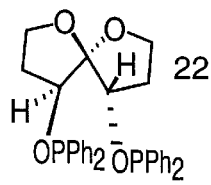
Figure 3:
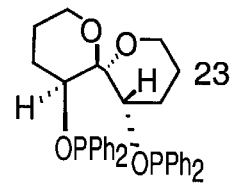

It is an objective of the present invention to provide a chiral diphosphine ligand that provides high enantioselectivity and activity. The present invention therefore provides a chiral phosphine ligand having a conformationally rigid cyclic structure, in which the phosphorus may be bonded to or be part of the cyclic structure. As such, the ligand rigidity provides enhanced chiral discrimination in metal catalyzed asymmetric organic reactions. In one embodiment, a "type I" or "type II" chiral bidentate phosphine ligand having a 2,2'-bis(diorganophosphino)-1,1'-bis(cyclic) structure wherein each cycle of the bis(cyclic) structure comprises 3 to 8 carbon atoms wherein the 1, 1', 2 and 2' carbon atoms in the bis(cyclic) structure are saturated carbon atoms and wherein the carbon atoms in the bis(cyclic) structure other than the 1, 1', 2 and 2' carbon atoms are optionally replaced with a heteroatom including but not limited to nitrogen, oxygen or sulfur; and wherein type II ligands have nitrogen in the 2,2' position, is provided.

In another embodiment, a "type III" chiral bidentate phosphine ligand having a 1,1'-bis(cyclic)-2,2' (organophosphinite) structure is provided.

In yet another embodiment, a "type IV" chiral phosphine ligand having a heteroatom-containing spiro bis-organophosphine or organophosphinite is provided.

In one embodiment, a "type V" chiral bidentate phosphine ligand having a (bis)phospha-tricyclic structure with a bridge group is provided.

In another embodiment, a "type VI" chiral phosphine ligand having a (bis)fused phospha-bicyclic structure comprising a bridge structure is provided.

In yet another embodiment, a "type VIIa" chiral phosphine ligand having a cis(bis) phosphine fused bicyclic structure is provided.

In one embodiment, a "type VIIb" chiral phosphine ligand having a cis or trans biphosphine cyclic structure having two R' substituents where R' is alkyl, fluoroalkyl or perfluoroalkyl (each having up to 8 carbon atoms), aryl, substituted aryl, arylalkyl, ring-substituted arylalkyl, and —$CR'_2(CR'_2)_q Z(CR'_2)_p R'$ where q and p are the same or different integers ranging from 1 to 8 and Z is defined as O, S, NR, PR, AsR, SbR, divalent aryl, divalent fused aryl, divalent 5-membered ring heterocyclic group, or a divalent fused heterocyclic group where R is alkyl of 1–8 carbon atoms, aryl, or substituted aryl is provided. In another embodiment, a "type VIIc" chiral phosphine ligand having a trans(bis) phosphine bicyclic structure.

In yet another embodiment, a "type V" chiral monodentate phosphine ligand comprising a phospha-tricyclic structure is provided.

And, in yet another embodiment, a "type VI" chiral monodentate phosphine ligand comprising a phospha-bicyclic structure is provided.

And, in yet another embodiment, a cyclic phosphine ligand having a structure of:

A. Bidentate cyclic chiral phosphines:

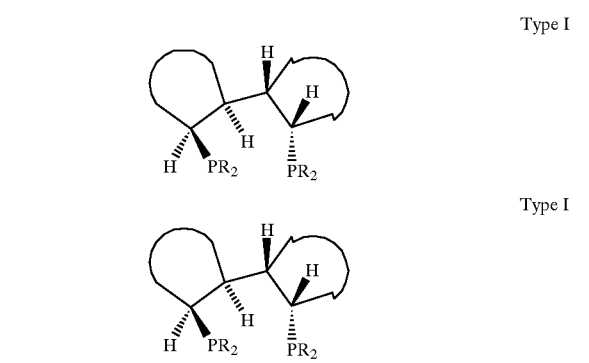

Type I

Type I

-continued

Type III

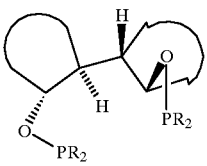

Type II

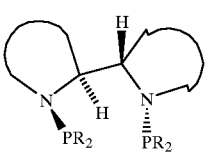

Type IV

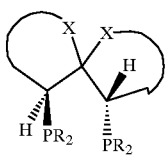

Type IV

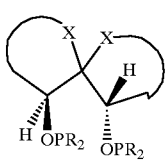

Type V

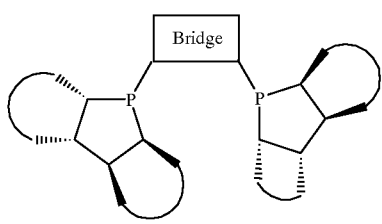

Type VI

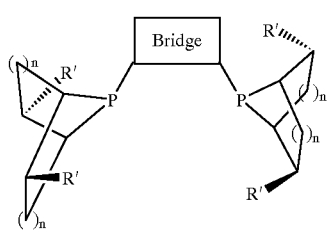

Type VIIa

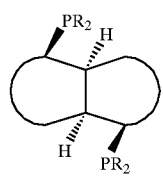

Type VIIb

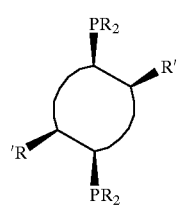

-continued

Type VIIb

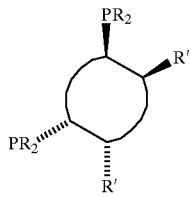

Type VIIc

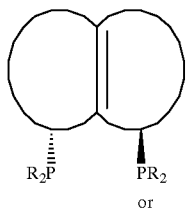

or

B. monodentate cyclic chiral phosphines

Type V

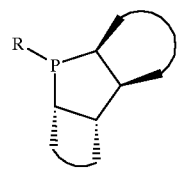

Type VI

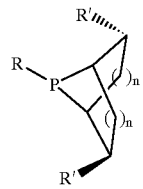

where each R is independently alkyl of 1–8 carbon atoms, substituted alkyl, aryl, or substituted aryl; each R' is independently alkyl, fluoroalkyl and perfluoroalkyl, each having up to 8 carbon atoms; aryl; substituted aryl; arylalkyl; ring-substituted arylalkyl; and —CR'$_2$(CR'$_2$)$_q$Z(CR'$_2$)$_p$R' wherein q and p are the same or different integers ranging from 1 to 8, R' is as defined above, and Z is selected from the group consisting of O, S, NR, PR, AsR, SbR, divalent aryl, divalent fused aryl, divalent 5-membered ring heterocyclic group, and a divalent fused heterocyclic group where R is as defined above; the cyclic structure D represents a ring having 3 to 8 carbon atoms which may be substituted within the ring with one or more oxygen, sulfur, N—R', C=O, or CR'$_2$; ° represents 0 to 8 carbon atoms; and where the ring may further be substituted with R' as defined above; the Bridge is —(CH$_2$)$_r$— where r is an integer ranging from 1 to 8; —(CH$_2$)$_s$Z(CH$_2$)$_m$— wherein s and m are each the same or different integers ranging from 1 to 8; 1,2-divalent phenyl; 2,2'divalent-1,1'biphenyl; 2,2'divalent 1,2'binapthyl; and ferrocene; each of which may be substituted with R' as defined above; and where the substitution on 1,2-divalent phenyl, the ferrocene or biaryl bridge is independently hydrogen, halogen, alkyl, alkoxyl, aryl, aryloxy, nitro, amino, vinyl, substituted vinyl, alkynyl, or sulfonic acid; X is O, S or NR where R is as defined above; and n is 1 or 2.

It is yet another objective of the present invention to provide a catalyst that provides high enantioselectivity and activity; in one embodiment of the present invention, a chiral phosphine ligand as described above complexed with a transition metal, preferably rhodium, iridium, ruthenium, palladium or platinium is provided.

In certain compounds of the present invention, the phosphine ligand is attached to an organic substrate or backbone by a chemical bridging group or organic substituent. For these compounds, it is preferred that the chemical bridging group or organic substituent has a linker to a polymer. The polymer-supported catalyst is a heterogenous or homogenous catalyst, dependent upon the solubility of the polymer in the reaction medium.

It is another objective of the present invention to provide a method for transition metal complex catalyzed asymmetric hydrogenation of ketones, imines, or olefin; in one embodiment, a method is provided in which such a reaction is catalyzed by a chiral phosphine ligand as described above complexed with a transition metal, preferably rhodium, iridium, ruthenium, palladium or platinium is provided.

Figure 4:
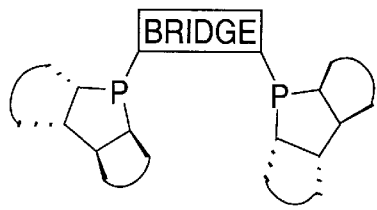
FIG. 4 depicts ligands 24–34 (Type V), chiral phosphines with phospha-tricyclic structures.
Figure 4:
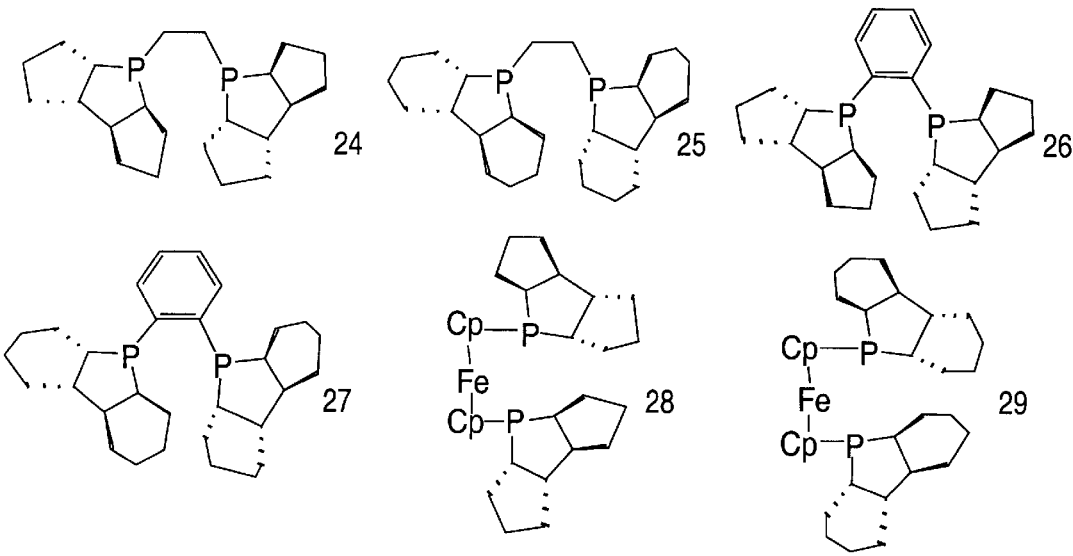
Figure 4:
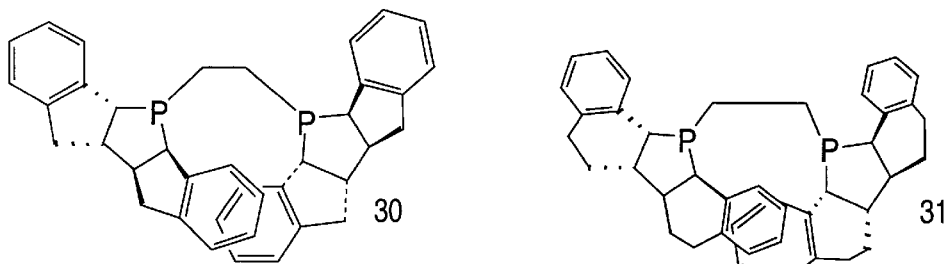
Figure 4:
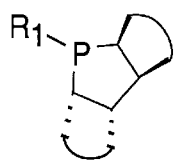
Figure 4:
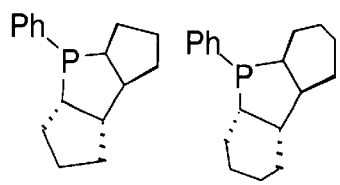
Figure 4:
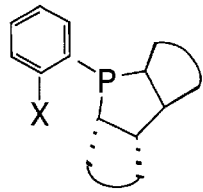
Figure 5:
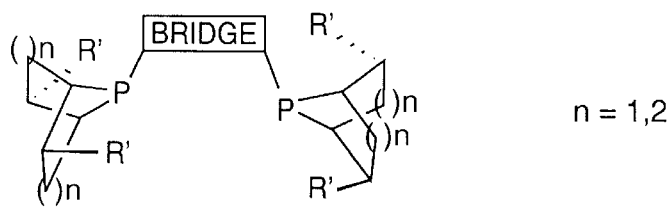
FIGS. 5 and 6 illustrate type VI chiral phosphines with fused phospha-bicyclic structures.
Figure 5:
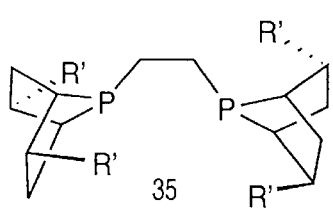
Figure 5:
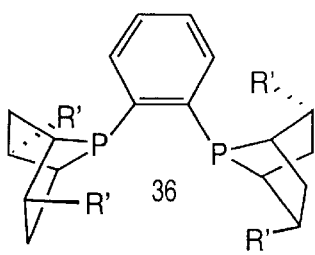
Figure 5:
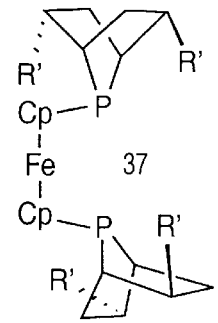
Figure 5:
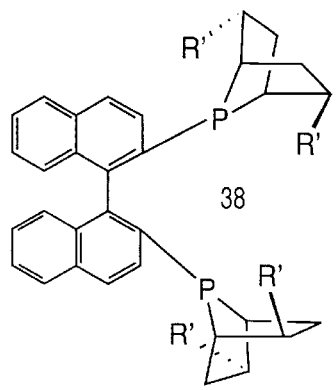
Figure 5:
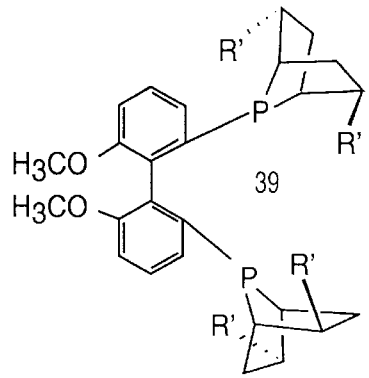
Figure 6:
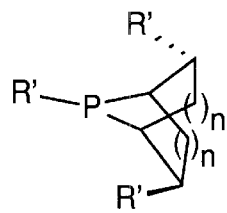
Figure 6:
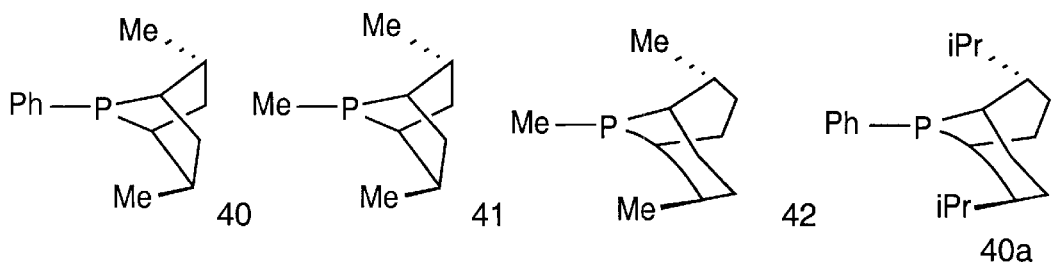
Figure 6:
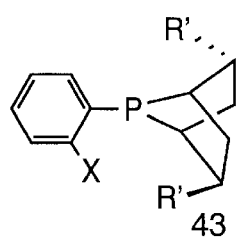
Figure 6:
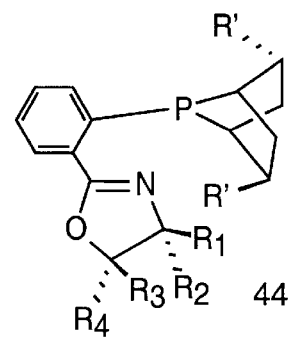
Figure 7:
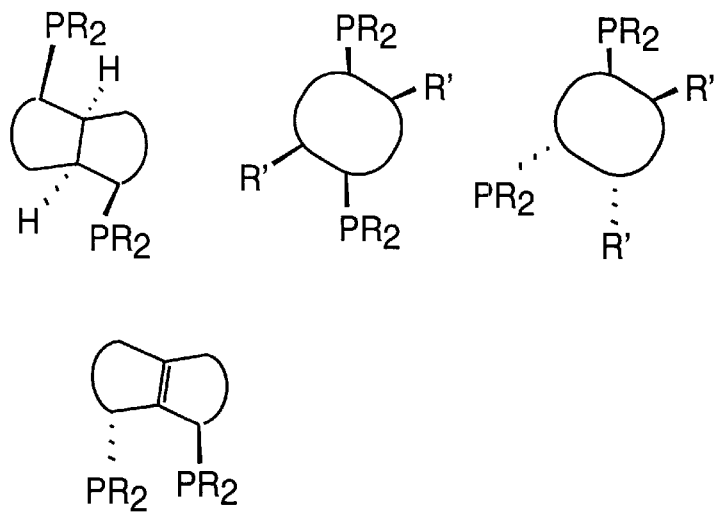
FIG. 7 shows type VII chiral phosphine ligands having one or two rings in their backbones.
Figure 7:
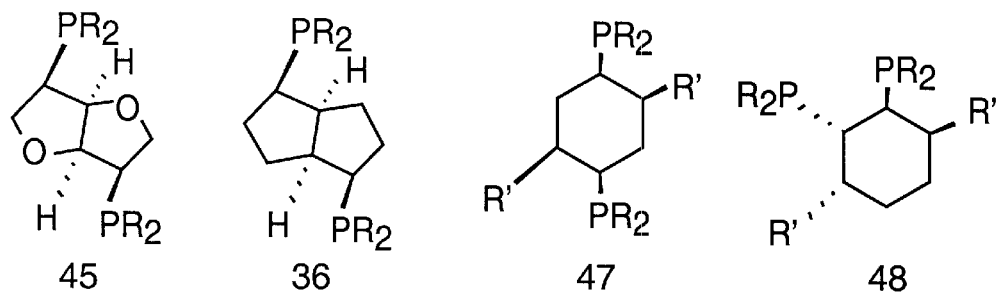
Figure 7:
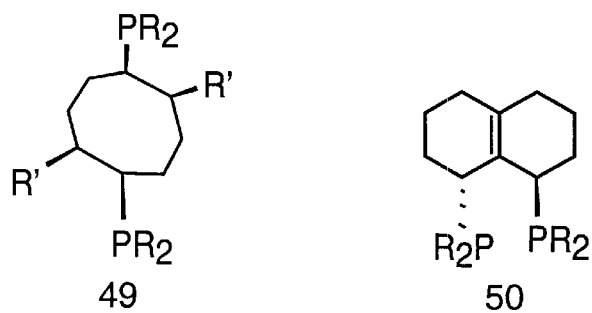

It is yet another objective of the present invention to provide an improved method for a transition metal catalyzed asymmetric reaction such as hydrogenation, hydride transfer reaction, hydrosilylation, hydroboration, hydrovinylation, hydrofornylation, hydrocarboxylation, allylic alkylation, cyclopropanation, Diels-Alder reaction, Aldol reaction, Heck reaction, Michael addition, and stereo-selective polymerization in one embodiment, the improvement comprising catalysing the reaction with a catalyst that is a chiral phosphine ligand as described above complexed with a transition metal, preferably rhodium, iridium, ruthenium, palladium or platinium. In yet another embodiment, the catalyst is selected from the group consisting of compound 1 as illustrated in FIG. 1, compound 36 as illustrated in FIG. 5, compound 40 as illustrated in FIG. 6, and compound 26 as illustrated in FIG. 4. In another embodiment, the catalyst is a complex of a chiral phosphine complexed with a compound that is [Rh(COD)Cl]$_2$, [Rh(COD)$_2$]X (X=BF$_4$, ClO$_4$, SbF$_6$, CF$_3$SO$_3$), [Ir(COD)Cl]$_2$, [Ir(COD)$_2$]X (X=BF$_4$, ClO$_4$, SbF$_6$, CF$_3$SO$_3$,), Ru(COD)Cl$_2$, [Pd(CH$_3$CN)$_4$[BF$_4$]$_2$, Pd$_2$(dba)$_3$ and [Pd(C$_3$H$_5$)Cl]$_2$. And, in yet another embodiment, the catalyst is Ru(RCOO)$_2$(Y), RuX$_2$(Y), Ru(methylallyl)$_2$(Y), Ru(aryl group)X$_2$(Y), where where X is Cl, Br or I and Y is a chiral diphosphine of the present invention.

It is yet another objective of the present invention to provide an improved method for asymmetric hydration of a ketone, imine or olefin catalyzed by a complex comprising Ru, Rh and kr and a chiral ligand; in one embodiment, the improvement includes conducting the catalysis with a palladium complex having a chiral phosphine ligand as described above. In yet another embodiment, the catalyst is selected from the group consisting of compound 1 as illustrated in FIG. 1, compound 36 as illustrated in FIG. 5, and compound 26 as illustrated in FIG. 4.

It is another method of the present invention to provide an improved method for asymmetric allyllic alkylation catalyzed by a complex comprising palladium and a chiral ligand; in one embodiment, the improvement includes catalysis with a palladium complex having a chiral ligand as described above. In yet another embodiment, the catalyst includes compound 40 as illustrated in FIG. 6.

It is yet another objective of the present invention to provide an intermediate for synthesis of a chiral phosphine ligand. In one embodiment, the intermediate shown as compound 3 in Scheme 2 is provided.

DETAILED DESCRIPTION

In the description of the cyclic chiral phosphine ligands above the term aryl includes phenyl, furan, thiophene, pyridine, pyrole, naphthyl and similar aromatic rings. Substituted aryl and substituted vinyl refer to an aryl or vinyl, respectively, substituted with one or more alkyl groups having 1–8 carbon atoms, alkoxy having 1–8 carbon atoms, alkylcarbonyl having 1–8 carbon atoms, carboxy, alkoxycarbonyl having 2–8 carbon atoms, halo (Cl, Br, F or I) amino, alkylamino or dialkylamino.

A suitable aryl, divalent aryl or divalent fused aryl for use in the present invention includes but is not limited to those derived from the parent compound benzene, anthracene or fluorene. A suitable 5-membered ring heterocyclic group for use herein includes but is not limited to one derived from the parent heterocyclic compound furan, thiophene, pyrrole, tetrahydrofuran, tetrahydrothiopene, pyrrolidine, arsole or phosphole. A suitable fused heterocyclic group for use herein includes but is not limited to one derived from the parent compound bipyridine, carbazole, benzofuran, indole, benzpyrazole, benzopyran, benzopyronone or benzodiazine. A suitable aryloxy group for use in the present invention includes but is not limited to an aryl having an oxygen atom as a substituent.

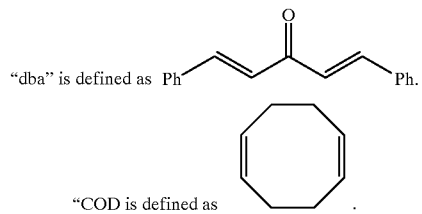

"dba" is defined as Ph~~~Ph.

"COD is defined as"

Alkyls having 1–8 carbon atoms includes straight or branched chain alkyls and cycloalkyls having 3 to 8 carbon atoms. Representative examples are methyl, ethyl, propyl, isopropyl, butyl, tertiary butyl, pentyl, cyclopentyl, hexyl cyclohexyl and the like. The alkyl group may be substituted with phenyl, substituted phenyl or alkoxy, carboxy, alkyoxycarbonyl, halo, amino, or alkyl amino or dialkylamino as defined above.

Certain compounds of the present invention provide a phosphine ligand attached to an organic substrate or backbone. In such cases, the chemical bridging group or the allyl or akyl groups adjacent to phosphine may include a linker to a polymer; the polymer supported-catalyst is a heterogenous or homogenous catalyst dependent upon the solubility of the polymer in the reaction medium.

Those skilled in the chemical art will recognize a wide variety of equivalent substituents.

The cyclic chiral phosphine ligands of the present invention are reacted with transistion metals to form catalyst. Preferably Group VIII transition metals are used and most preferably the catalyst is formed with rhodium, iridium, ruthenium, or palladium.

The invention encompasses a variety of asymmetric reactions utilizing catalyst of the invention, such as hydrogenation, hydride transfer, hydrosilylation, Grignard Cross-coupling, hydrocyanation, isomerisation, cycloadditions, Sigmatropic rearrangement, hydroboration, hydroformylation, hydrocarboxylation, allylic alkylation, hydrovinylation, cyclopropanation, aldol reaction, Heck reaction, Michael addition, and stereo-selective polymerization can be carried out with these ligand systems. The catalyst of this invention provides efficient and practical methods for producing chiral drugs for antihypertensive, antihistamine, cardiovascular and central nervous system therapies. The transition metal complexes of cyclic chiral phosphine ligands of the present invention are also important in the production of chiral agrochemicals.

The invention is illustrated by the synthesis and application of a chiral 1,4-bisphosphine, (2R,2'R)-bis(diphenylphosphino)-(1R,1'R)-dicyclopentane (1) (abbreviated (R, R)-BICP) (Scheme 2) in the rhodium catalyzed asymmetric hydrogenation of α-(acylamino) acrylic acids. An important feature of this ligand is that it contains two cyclopentane rings in its backbone which are present to restrict its conformational flexibility leading to high enantioselectivity in asymmetric reactions.

Scheme 1

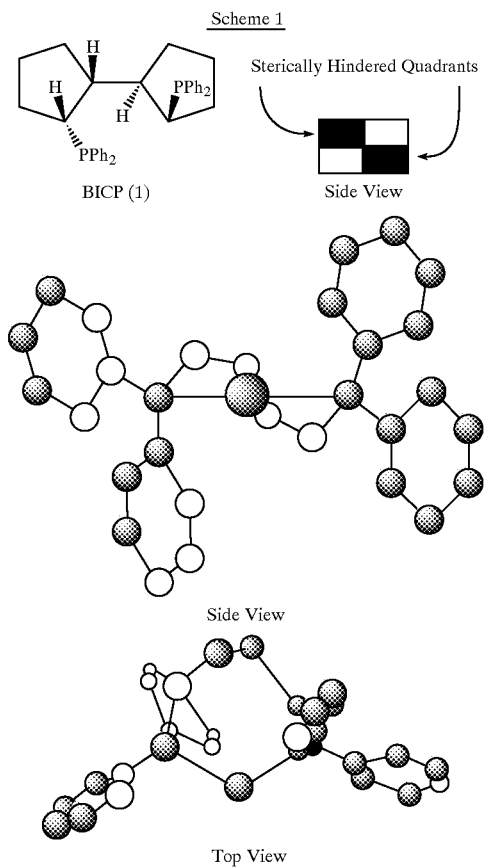

Side View

Top View

The bisphosphine ligand (1, R, R-BICP) was synthesized from readily available 1,1'-dicyclopentene (2)[11] as shown in Scheme 2. Asymmetric hydroboration of 2 using (+)-monoisopinocamphenylborane [(+) IpcBH$_2$] followed by oxidation with H$_2$O$_2$[12] gave the desired chiral diol (3) (100% ee after recrystallization from ether/hexanes), which was then converted to the dimesylate in high yield. Subsequent reaction of the dimesylate with lithium diphenylphosphine afforded the bisphosphine 1.

Scheme 2

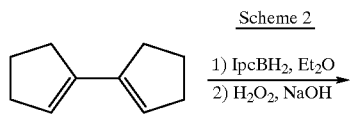

-continued

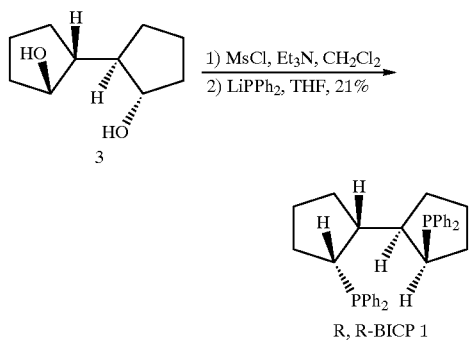

R, R-BICP 1

Hydrogenation of α-acetoamidocinnamnic acid was carried out at rt and 1 atm of hydrogen in the presence of the catalyst formed in situ from [Rh(COD)$_2$]BF$_4$ and bisphosphine 1 (1:1.1). Table 1 shows the results of hydrogenation of α-acetoamidocinnamic acid under a variety of conditions. The addition of a catalytic amount of triethylamine (Rh:1:Et$_3$N=1:1.1:50) gave a better optical yield than without triethylamine (Entry 1 vs 2). This effect may be due to a conformational change in the chiral Rh complex, since the carboxylate anion generated from the substrate and triethylamine has a greater affinity for the metal than the corresponding acid.[9a] The enantioselectivity in the hydrogenation was found to be highly dependent on the nature of the Rh complex. When a neutral Rh complex was used as the catalyst precursor, the optical yield decreased dramatically (entry 3). The highest selectivity (96.8%, S) for the hydrogenation of a-acetoamidocinnanic acid was obtained in THF at 1 atm of H$_2$ in the presence of triethylamine (entry 4), while changing substrate/catalyst ratio had a small effect on the enantioselectivities (entry 4 vs 5).

TABLE 1

Optimization of the asymmetric hydrogenation of α-acetamidocinnamic acid[a]

| Entry | Solvent | Et$_3$N (%) | ee (%)[b] |
|---|---|---|---|
| 1 | EtOH | — | 89.2 |
| 2 | EtOH | 50 | 93.3 |
| 3[c] | EtOH | 50 | 83.6 |
| 4 | ClCH$_2$CH$_2$Cl | 50 | 93.4 |
| 5 | THF | 50 | 96.8 |
| 6[d] | THF | 5 | 95.1 |

[a]The reaction was carried out at rt under 1 atm of H$_2$ for 24 h [substrate (0.5 mmol, 0.125 M):[Rh(COD)$_2$]BF$_4$:ligand(1) = 1:0.01:0.011]. The reaction went in quantitative yield.
[b]Determined by GC using aChirasil-VAL III FSOT column on the corresponding methyl ester. The S absolute configuration was determined by comparing the optical rotation with the reported value.
[c]0.5 mol % [Rh(COD)Cl]$_2$ was used as the catalyst precursor.
[d]0.1 mol % [Rh(COD)$_2$]BF$_4$/0.11 mol % ligand (1)/5 mol % Et$_3$N were used.

The methology is useful in the asymmetric synthesis of chiral amino acids. Tables 2 and 3 show the enantioselectivity of some amino acids obtained by hydrogenation of α-(acylamino)acrylic acids under an optimum condition. Enantioselectivities in this hydrogenation were not sensitive to the substitution pattern on the β-position of the prochiral olefin substrates, where α-benzamidocinnamic acid gave better optical than the corresponding acetoamido derivative.

TABLE 2

Asymmetric Hydrogenations of Dehydroamino Acid Derivatives

R–CH=C(COOH)(NHCOR') + H$_2$ (1 atm) $\xrightarrow[\text{THF, rt, 24 h}]{\text{[Rh(COD)}_2\text{]BF}_4\text{(1 mol \%)}\;\text{BICP(1.1 mol \%), Et}_3\text{N(50 mol \%)}}$ R–CH$_2$–CH(COOH)(NHCOR') (S)

| Entry | Substrate | Con. % | % ee[a] |
|---|---|---|---|
| 1 | CH$_2$=C(COOH)(NHCOCH$_3$) | 100 | 97.5 |
| 2 | i-Pr-CH=C(COOH)(NHCOCH$_3$) | 100 | 92.6 |
| 3 | Ph-CH=C(COOH)(NHCOCH$_3$) | 100 | 96.8 |
| 4 | Ph-CH=C(COOH)(NHCOPh) | 100 | 99.0 |
| 5 | 3-Br-C$_6$H$_4$-CH=C(COOH)(NHCOCH$_3$) | 100 | 97.0 |

[a] % ee determined by GC using Chirasil-VAL III FSOT Column of the corresponding methyl ester.

TABLE 3

Asymmetric Hydrogenations of Dehydroamino Acid Derivatives

R–CH=C(COOH)(NHCOR') + H$_2$ (1 atm) $\xrightarrow[\text{THF, rt, 24 h}]{\text{[Rh(COD)}_2\text{]BF}_4\text{(1 mol \%)}\;\text{BICP(1.1 mol \%), Et}_3\text{N(50 mol \%)}}$ R–CH$_2$–CH(COOH)(NHCOR') (S)

| Entry | Substrate | Con. % | % ee[a] |
|---|---|---|---|
| 6 | 4-MeO-C$_6$H$_4$-CH=C(COOH)(NHCOCH$_3$) | 100 | 99.0 |
| 7 | 3-MeO-4-AcO-C$_6$H$_3$-CH=C(COOH)(NHCOCH$_3$) | 100 | 98.2 |
| 8 | 2-Cl-C$_6$H$_4$-CH=C(COOH)(NHCOCH$_3$) | 100 | 92.5 |
| 9 | 4-F-C$_6$H$_4$-CH=C(COOH)(NHCOCH$_3$) | 100 | 91.6 |
| 10 | 2-Naphthyl-CH=C(COOH)(NHCOCH$_3$) | 100 | 92.9 |

[a] % ee determined by GC using Chirasil-VAL III FSOT Column of the corresponding methyl ester or by HPLC (OJ collumn)

For the corresponding methyl ester, the results are summarized in Table 4.

TABLE 4

Asymmetric Hydrogenations of Methyl Ester of Dehydroamino Acid Derivatives

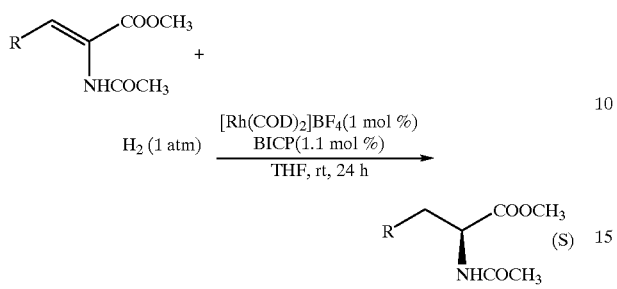

| Entry | Substrate (R) | Con. % | % ee[a] |
|---|---|---|---|
| 1 | H | 100 | 76.2 |
| 2 | phenyl | 100 | 78.4 |
| 3[b] | phenyl | 100 | 60.0 |
| 4 | 3-bromophenyl | 100 | 75.1 |
| 5 | 4-fluorophenyl | 100 | 80.5 |

TABLE 4-continued

Asymmetric Hydrogenations of Methyl Ester of Dehydroamino Acid Derivatives

| Entry | Substrate (R) | Con. % | % ee[a] |
|---|---|---|---|
| 6 | 2-chlorophenyl | 100 | 70.9 |
| 7 | 2-naphthyl | 100 | 85.3 |
| 8 | 2-thienyl | 100 | 79.1 |

[a]ee determined by GC using Chirasil-VAL III FSOT Column
[b]50 mol % Et$_3$N was added Table 5 illustrates comparative asymmetric hydrogenations of dehydroamino acid derivatives.

TABLE 5

Asymmetric Hydrogenations of Dehydroamino Acid Derivatives $$\underset{\text{R}}{\overset{\text{COOH}}{\diagup}}\!\!\!\!\!\!\!\!\diagdown\underset{\text{NHCOR}}{} \quad \xrightarrow[\text{H}_2 \; X = BF_4^-, ClO_4^-]{Rh(COD)(P-P)X} \quad \underset{\text{R}}{}\overset{\text{COOH}}{\diagup}\!\!\!\diagdown\underset{\text{NHCOR}}{}$$

P—P = chiral diphenylphosphine (% ee)

| Substrate | DiPAMP | BINAP | CHIRAPHOS | BPPM | DIOP | BICP |
|---|---|---|---|---|---|---|
| CH$_2$=C(COOH)(NHCOCH$_3$) | 94 | 67 | 91 | 98 | 73 | 98 |

TABLE 5-continued

Asymmetric Hydrogenations of Dehydroamino Acid Derivatives

R–CH=C(COOH)(NHCOR) + H₂ →[Rh(COD)(P—P)X, X = BF₄⁻, ClO₄⁻]→ R–CH₂–C*H(COOH)(NHCOR)

| Substrate | P—P = chiral diphenylphosphine (% ee) | | | | | |
|---|---|---|---|---|---|---|
| | DiPAMP | BINAP | CHIRAPHOS | BPPM | DIOP | BICP |
| Ph–CH=C(COOH)(NHCOCH₃) | 95 | 84 | 89 | 91 | 81 | 97 |
| Ph–CH=C(COOH)(NHCOPh) | 96 | 100 | 99 | 83 | 64 | 99 |
| (H₃CO)(AcO)C₆H₃–CH=C(COOH)(NHCOCH₃) | 94 | 79* | 83 | 86 | 84 | 98 |

*NHCOPh

For the asymmetric hydrogenation of imines, rhodium iridium-complexes of BICP are effective. Table 6 provides some results on this asymmetric reaction. For an imine substrate, up to 94% ee has achieved and this is among the highest enantioselectivity obtained with group VIII transition metal catalysts coordinated by a chiral phosphine ligand.

TABLE 6

Ir and Rh-Catalyzed Asymmetric Hydrogenation of Imines

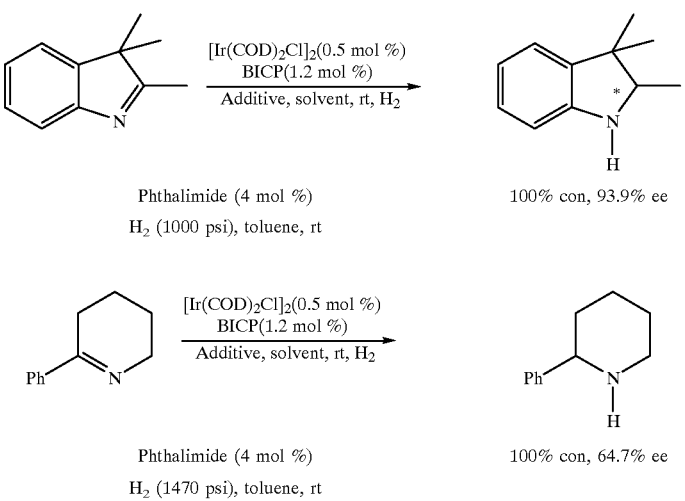

TABLE 6-continued

Ir and Rh-Catalyzed Asymmetric Hydrogenation of Imines

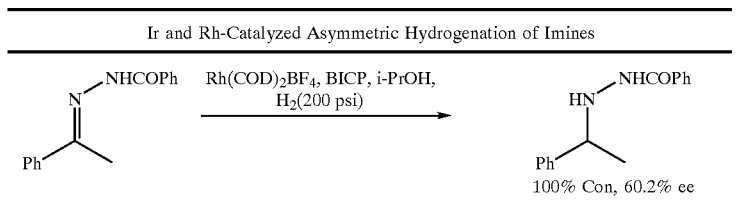

100% Con, 60.2% ee

The rigid fused bicyclic [2.2.1] structure represents a new motif in chiral ligand design. Changes in the size of the R group on the ring system can modulate the asymmetric induction and high enantioselectivities can be achieved. Scheme 3 shows the synthesis of new chiral bicyclic phosphines (abbreviated as PennPhos because it represents a different structure from DuPhos [DuPont Phosphine] and was made at Penn State).

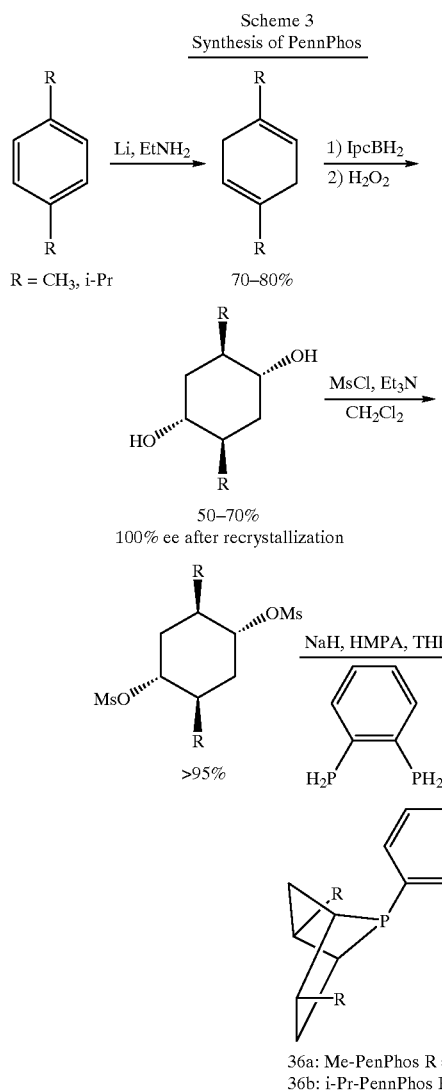

Rhodium complexes with PennPhos ligands can be used as catalyts for asymmetric hydrogenation. Table 7 lists the asymmetric hydrogenation results for dehydroamino acid derivatives.

TABLE 7

Asymmetric Hydrogenations of Dehyroamino Acid Derivatives

R—CH=C(NHCOR')—COOH + H$_2$ (1 atm) $\xrightarrow[\text{THF, rt, 1-24 h}]{\substack{[Rh(COD)_2]BF_4 (1 \text{ mol \%}) \\ L(1.1 \text{ mol \%})}}$ R—CH$_2$—*CH(NHCOR')—COOH (R)

L = Me-Penn Phos

| Entry | Substrate | Con. % | % ee[a] |
|---|---|---|---|
| 1 | Ph-CH=C(NHCOCH$_3$)-COOH | 100 | 84.3 |
| 2 | Ph-CH=C(NHCOPh)-COOH | 100 | 52.8 |
| 3 | (3-Br-C$_6$H$_4$)-CH=C(NHCOCH$_3$)-COOH | 100 | 82.7 |
| 4 | (2-Cl-C$_6$H$_4$)-CH=C(NHCOCH$_3$)-COOH | 100 | 82.3 |

TABLE 7-continued

Asymmetric Hydrogenations of Dehyroamino Acid Derivatives

| 5 | (4-F-C₆H₄)CH=C(COOH)(NHCOCH₃) | 100 | 81.9 |
| 6 | (2-naphthyl)CH=C(COOH)(NHCOCH₃) | 100 | 83.5 |

[a] % ee determined by GC using Chirasil-VAL III FSOT Column of the corresponding methyl ester.

The rhodium complexes with Me-Pennphos are very effective for hydrogenation of simple ketones. Up to 97% ee has been obtained with acetophenone, which is the highest enantioselectivity reported in the direct asymmetric hydrogenation of simple ketones with group VIII transition metal complexes. Table 8 summarizes some results for this study.

TABLE 8

Asymmetric Hydrogenations of Simple Ketones $$R_1-CO-R_2 + H_2 \xrightarrow[\text{MeOH}]{\substack{[Rh(COD)_2]BF_4(1\text{ mol \%}) \text{ or} \\ [Rh(COD)Cl]_2 \\ L(1.1\text{ mol \%})}} R_1-CH(OH)-R_2$$

L = Me-Penn Phos

| Entry | Substrate | Catalyst | H₂ Pressure | Con. % | % ee |
|---|---|---|---|---|---|
| 1 | acetophenone | [Rh(COD)Cl]₂ | 30 atm | 97 | 96.5 |
| 2 | 2-acetonaphthone | [Rh(COD)Cl]₂ | 30 atm | 70 | 91 |

TABLE 8-continued

Asymmetric Hydrogenations of Simple Ketones

| | | | | | |
|---|---|---|---|---|---|
| 3 | ![acetophenone] | [Rh(COD)₂]BF₄ | 70 atm | 73 | 79.6 |

Synthesis of another class of chiral cyclic phosphines is illustrated in Scheme 4. The phospha-tricyclic structure is unique and the phosphines are made from chiral 1,4-diols with two rings. Tricyclic structure dictates the chiral environment around phosphines and ring size can be changed by varing the chiral diols. Both monophosphines and bisphosphines can be made from the straightforward synthetic route. They can be used as ligands for many asymmetric reactions

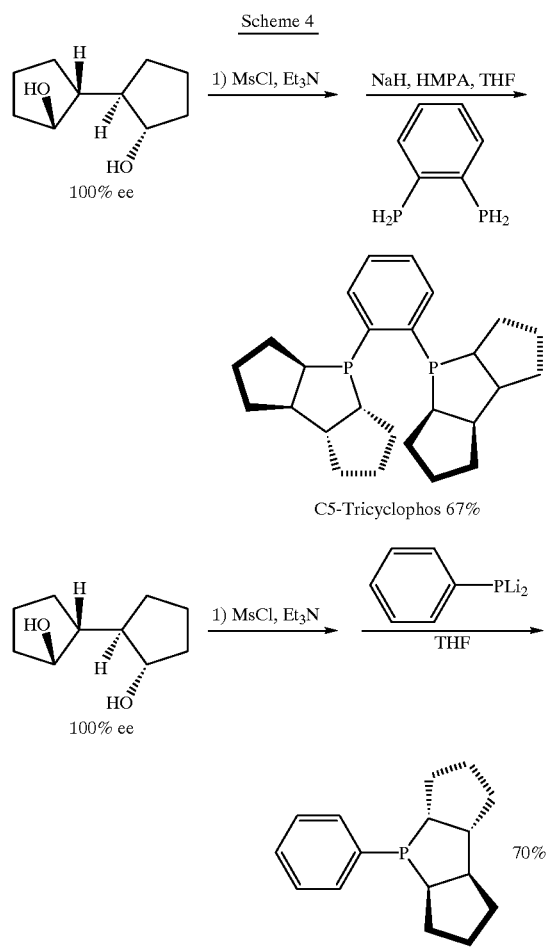

Scheme 4

Rhodium complexes with these chiral tricyclic phosphines can be used as catalyts for asymmetric hydrogenation. Table 9 lists the asymmetric hydrogenation results for dehydroamino acid derivatives.

TABLE 9

Asymmetric Hydrogenations of Dehyroamino Acid Derivatives

| Entry | Substrate | Con. % | % ee[a] |
|---|---|---|---|
| 1 | Ph-CH=C(NHCOCH₃)COOH | 100 | 52.9 |
| 2 | Ph-CH=C(NHCOCH₃)COOMe | 100 | 77.6 |

[a]ee determined by GC using Chirasil-VAL III FSOT Column of the corresponding methyl ester.

The rigid fused bicyclic [2.2.1] structure represents a new motif in chiral ligand design. Analogous to Burk's systems, changes in the size of the R group on the ring system can modulate the asynimetric induction and high enantioselectivities can be achieved. The present invention provides the syntheses of chiral monophosphines with this fused bicyclic ring structure (Scheme 5) and their application in Pd-catalyzed asymmetric allylic alkylations.

Scheme 5

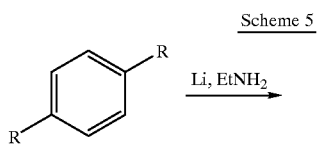

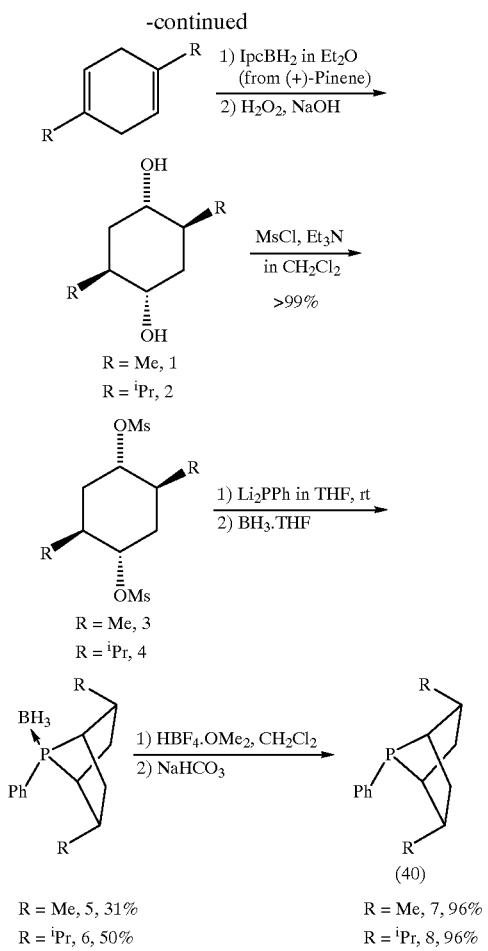

The ligand synthesis depends on the availability of enantiomerically pure cyclic 1,4-diols. Halterman[13] and Vollhardt[14] have previously prepared chiral cyclopentadiene derivatives from the chiral diols.[13-14] Halterman[13] has synthesized chiral diols 1 and 2 from the inexpensive starting materials p-xylene and p-diisopropylbenzene, respectively. The synthesis employed Birch reduction, followed by asymmetric hydroboration and recrystallization to 100% ee. Conversion of the optically pure diols to the corresponding mesylates proceeds cleanly. Nucleophilic substitution by $Li_2PPh$ on the chiral dimesylates 3 and 4 generated the corresponding bicyclic phosphines, which were trapped by $BH_3.TH$ to form the air-stable boron-protected monophosphines 5 and 6, respectively. Deprotection with a strong acid produces the desired products [7, (1R,2S, 4R,5S)-(+)-2,5-dimethyl-7-phenyl-7-phosphabicyclo[2.2.1]heptane; 8, (1R, 2R, 5R)-(+)-2,5-diisopropyl-7-phenyl-7-phosphabicyclo-[2.2.1]heptane] in high yields.

Pd-catalyzed allylic alkylation was utilized to test the effectiveness of these new monophosphines as chiral ligands. Although many palladium complexes of multidentate phosphine and nitrogen ligands are excellent catalysts for this reaction,[15] palladium complexes of simple chiral monophosphines are normally not effective.[15] However, Pd-catalyzed allylic alkylation with the new monophosphine 7 gave excellent enantioselectivities and conversions (Table 10), comparable to the best results (99% ee) reported to date.[15]

TABLE 10

Palladium-Catalyzed Asymmetric Allyclic Alkylation with Chiral Monophosphines[a]

| Entry | L* | [Pd] | [Pd]:L* | Nu | Additive | Time (h) | Yield (%) | % ee[b] |
|---|---|---|---|---|---|---|---|---|
| 1 | 7 | $Pd_2(dba)_3$ | 1:2.2 | $CH_2(CO_2Me)_2$ | — | 1.5 | 96 | 74(R) |
| 2 | 7 | $Pd(OAc)_2$ | 1:2.2 | $CH_2(CO_2Me)_2$ | — | 4.0 | 98 | 72(R) |
| 3 | 7 | $[Pd(C_3H_5)Cl]_2$ | 1:1.1 | $CH_2(CO_2Me)_2$ | — | 5.0 | 97 | 60(R) |
| 4 | 7 | $[Pd(C_3H_5)Cl]_2$ | 1:2.2 | $CH_2(CO_2Me)_2$ | — | 2.0 | 93 | 95(R) |
| 5 | 7 | $[Pd(C_3H_5)Cl]_2$ | 1:3.3 | $CH_2(CO_2Me)_2$ | — | 1.5 | 96 | 96(R) |
| 6 | 7 | $[Pd(C_3H_5)Cl]_2$ | 1:2.2 | $CH_2(CO_2Me)_2$ | 2.8% $AgBF_4$ | 1.0 | 80 | 97(R) |
| 7 | 7 | $[Pd(C_3H_5)Cl]_2$ | 1:2.2 | $CH_2(CO_2Me)_2$ | 2.8% LiCl | 2.0 | 95 | 96(R) |

TABLE 10-continued

Palladium-Catalyzed Asymmetric Allyclic Alkylation with Chiral Monophosphines[a]

| 8  | 7 | [Pd(C³H₅)Cl]₂ | 1:2.2 | CH₂(COMe)₂      | — | 2.0 | 99 | >97[c](R)   |
|----|---|---------------|-------|-----------------|---|-----|----|-------------|
| 9  | 7 | [Pd(C₃H₅)Cl]₂ | 1:2.2 | CH(NHAc)(CO₂Et)₂| — | 2.0 | 95 | >99.5[d](S) |
| 10 | 8 | [Pd(C₃H₅)Cl]₂ | 1:2.2 | CH₂(CO₂Me)₂     | — | 3.5 | 99 | 78(R)       |

[a]The reaction was carried out under N₂ using 1,3-diphenyl-2-propenyl acetate, Nu (nucleophile) (300 mol %), BSA (bis(trimethylsilyl)acetamide) (300 mol %), KOAc (2 mol %), toluene, [Pd] 1.4 mol % and L*.
[b]% ee was measured by HPLC using a Chiralcel OD column, and the absolute configuration was determined by comparing the optical rotation with literature values.
[c]% ee was measured by comparing the optical rotation with literature values.
[d]% ee was measured by HPLC using a Chiracel OJ column.

Ruthenium complexes with chiral phosphines are excellent catalysts for the asymmetric hydrogenation of beta keto-esters. Table 11 lists the results based on Ru-BICP catalytic system.

TABLE 11

Asymmetric Hydrogenations of beta-Keto ester

| Entry | Temp   | Catalyst    | H₂ Pressure | Con. % | % ee |
|-------|--------|-------------|-------------|--------|------|
| 1     | 65° C. | Ru(BICP)Br₂ | 1 atm       | 97     | 82   |
| 2     | 40° C. | Ru(BICP)Br₂ | 5 atm       | 95     | 76   |
| 3     | 50° C. | Ru(BICP)Cl₂ | 5 atm       | 43     | 84   |

EXAMPLES

Unless otherwise indicated, all reactions were carried out under nitrogen. THF and ether were freshly distilled from sodium benzophenone ketyl. Toluene and 1,4-dioxane were freshly distilled from sodium. Dichloromethane and hexane were freshly distilled from CaH₂. Methanol was distilled from magnesium and CaH₂. Reactions were monitored by thin-layer chromatography (TLC) analysis. Column chromatography was performed using EM silica gel 60 (230–400 mesh). ¹H NMR were recorded on Bruker ACE 200, WP 200, AM 300 and WM 360 spectrometers. Chemical shifts are reported in ppm downfield from tetramethylsilane with the solvent resonance as the internal standard (CDCl₃, δ 7.26 ppm). ¹³C, ³¹P and ¹H NMR spectra were recorded on Brnker AM 300 and WM 360 or Varian 200 or 500 spectrometers with complete proton decoupling. Chemical shifts are reported in ppm downfield from tetramethylsilane with the solvent resonance as the internal standard (CDCl₃, δ 77.0 ppm). Optical rotation was obtained on a Perkin-Elmer 241 polarimeter. MS spectra were recorded on a KRATOS mass spectrometer MS 9/50 for LR-EI and HR-EI. GC analysis were carried on Helwett-Packard 5890 gas chromatograph with a 30-m Supelco β-DEX™ or r-225Dex™ column. HPLC analysis were carried on Waters™ 600 chromatograph with a 25-cm CHIRALCEL OD column.

Example 1

(as depicted in Scheme 2 and FIG. 8)
(1R,1'R)-Bicyclopentyl-(2S,2'S)-diol
(3 in scheme 2)

Compound 3 was synthesized by asymmetric hydroboration of bi-1-cyclopentenlyl using (+)-monoisopinocampheylborane ((+)-IpcBH₂) according to the literature procedure (Brown, H. C.; Jadhav, P. K., Mandal, A. K. *J. Org. Chem.* 1982, 47, 5074). The absolute configuration of the diol was assigned based on the asymmetric hydroboration of trisubstituted olefins (e.g. methylcyclopentene) using (+)-IpcBH₂. ¹H NMR (CDCl₃, 300 MHz) δ 4.04(br, 2 H), 3.84 (m, 2 H), 2.02 (m, 2 H), 1.66–1.22 (m, 10 H), 1.21 (m, 2 H); ¹³C NMR δ 78.6, 52.2, 33.6, 29.2, 20.5; MS m/z 170 (M⁺, 0.35), 152, 134, 108, 95, 84, 68; HRMS calcd for C₁₀H₁₈O₂: 170.1307(M⁺); found: 170.13 15.

Example 2

(as depicted in Scheme 2 and FIG. 8)
(1R,1'R)-Bicyclopentyl-(2S,2'S)-diol bis (methanesulfioate)

To a solution of (1R,1'R)-bicyclopentyl-(2S, 2'S)-diol (0.8 g, 4.65 mmol) and triethylamine (1.68 mL, 12.09 mmol) in CH₂Cl₂ (30 mL) was added dropwise a solution of methanesulfonyl chloride (0.76 mL, 9.92 mmol) in CH₂Cl₂ (2 mL) at 0° C. The reaction mixture was stirred at 0° C. for 30 min, and at rt for 2 h, then quenched by saturated aqueous ammonium chloride solution (25 mL). The aqueous layer was extracted with CH₂Cl₂ (3×20 mL) and the combined organic solution was dried over Na₂SO₄. After evaporation of the solvent, a white solid was obtained, which was used directly for the next step. ¹H NMR (CDCl₃, 200 MHz) δ 5.01(m, 2H), 3.04 (s, 6 H), 2.17 (m, 2 H), 2.15–1.65 (m, 10 H), 1.43–1.52 (m, 2 H); ¹³C NMR δ 86.8, 48.2, 38.4, 32.8, 27.4, 22.5.

Example 3

(as depicted in Scheme 2 and FIG. 8)
(1R,1'R,2R,2'R)-1,1'-Bis(2-diphenylphosphino) cyclopentyl bisboranle Diphenylphosphine (1.25 mL, 7.0 mmol) in THF (80 mL) was cooled to −78° C. To this solution, n-BuLi in hexane (4.1 mL, 6.6 mmol) was added via syringe over 5 min. The resulting orange solution was warmed to rt and stirred for 30 min. After cooling the mixture to −78° C., (1R,1'R,2S,2'S)-1,1'-bicyclopentyl-2,2'-diol bismesylate (1.01 g, 3.1 mmol) in THF (20 mL) was added over 20 min. The resulting orange solution was warmed to rt and stirred overnight. The white suspension solution was hydrolyzed with saturated aqueous NH₄Cl solution. The aqueous layer was extracted with CH₂Cl₂ (2×20 mL). The combined organic solution was dried over anhydrous Na₂SO₄. After removal of the solvents under reduced pressure, the residue was dissolved in CH₂Cl₂ (50 mL), then treated with BH₃.THF (10 mL, 10 mmol) at rt and the mixture was stirred overnight. The reaction mixture was added to NH$_4$Cl aqueous solution, and extracted with CH$_2$Cl$_2$ (2×50 mL). The combined organic solution was dried over anhydrous Na$_2$SO$_4$. After evaporation of the solvent under reduced pressure, the residue was subjected to column chromatography on silica gel, eluting with CH$_2$Cl$_2$/hexane (1:5) and then CH$_2$Cl$_2$/hexane (2:3) affording the product as a white solid. Yield: 0.36 g (21%). $^1$H-NMR (CDCl$_3$) δ 7.80–7.30 (m, 20 H, Ph), 2.55–2.35 (m, 2 H, CHP(BH$_3$)Ph$_2$), 1.95–1.35 (m, 14 H, CH$_2$ and CH), 1.7–0.5 (broad, 6 H, BH$_3$). $^{31}$P-NMR (CDCl$_3$): δP=17.5 (br). $^{13}$C-NMR (CDCl$_3$) δ 133.43 (d, $^2$J(PC)=8.5 Hz, C$_{ortho}$), 132.25 (d, $^2$J(PC)=8.5 Hz, C$_{ortho}$), 132.08 (d, $^1$J(PH)=50.0 Hz, C$_{ipso}$), 130.67 (d, $^4$J(PC)=2.1 Hz, C$_{para}$), 130.57 (d, $^4$J(PC)=2.1 Hz, C$_{para}$), 129.71 (d, $^1$(PC)=56.5 Hz, C$_{ipso}$), 128.39 (d, $^3$J(PC)=9.4 Hz, C$_{meta}$), 128.29 (d, $^3$J(PC)=9.1 Hz, C$_{meta}$), 46.28 (dd, J(PC)=2.1 and 4.8 Hz, C$_{1,1}$), 36.26 (d, $^1$J(PC)=30.6 Hz, C$_{2,2}$), 31.19 (CH$_2$), 29.52 (CH$_2$), 22.51 (CH$_2$); MS m/z 520 (8.95), 506 (3.55), 429(19.10), 321 (100), 253(7.45), 185(26.64), 108(43.68), 91(11.99), 77(6.88), HRMS cacld for C$_{28}$H$_{31}$P$_2$ (M$^+$-B$_2$H$_6$-Ph): 429.1901, found: 429.1906.

Example 4

Figure 8:
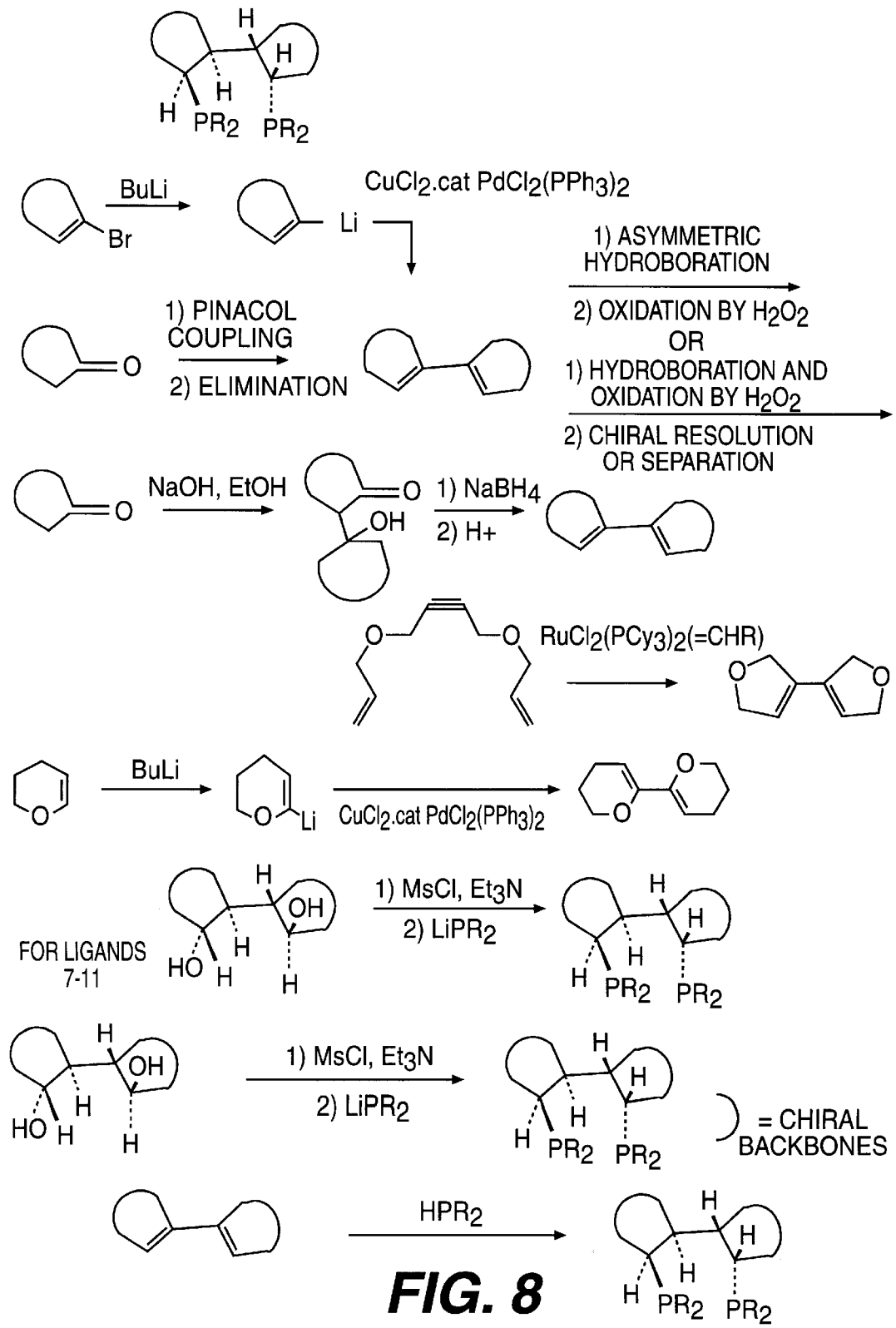
FIG. 8 outlines the synthesis of the type I ligands, 1–13. Asymmetric hydroboration of dienes or hydroboration of chiral dienes can lead to chiral 1,4-diols. Chiral resolution of diols can also provide an effective routes to chiral diols. Dienes and chiral dienes may be generated using variety of methods including but not limited to Pinacol coupling and elimination, aldol condensation followed by reduction and elimination, Methathesis, and coupling of vinyl halide or vinyl lithium. Mesylation of diols and nucleophilic attack of mesylates with a variety of phosphides can produce the desired products. With chiral dienes, the free-radical addition of $HPR_2$ may lead to the products. For the inversion of the chiral diol, Mitsunobo reaction may be applied.
Figure 8A:
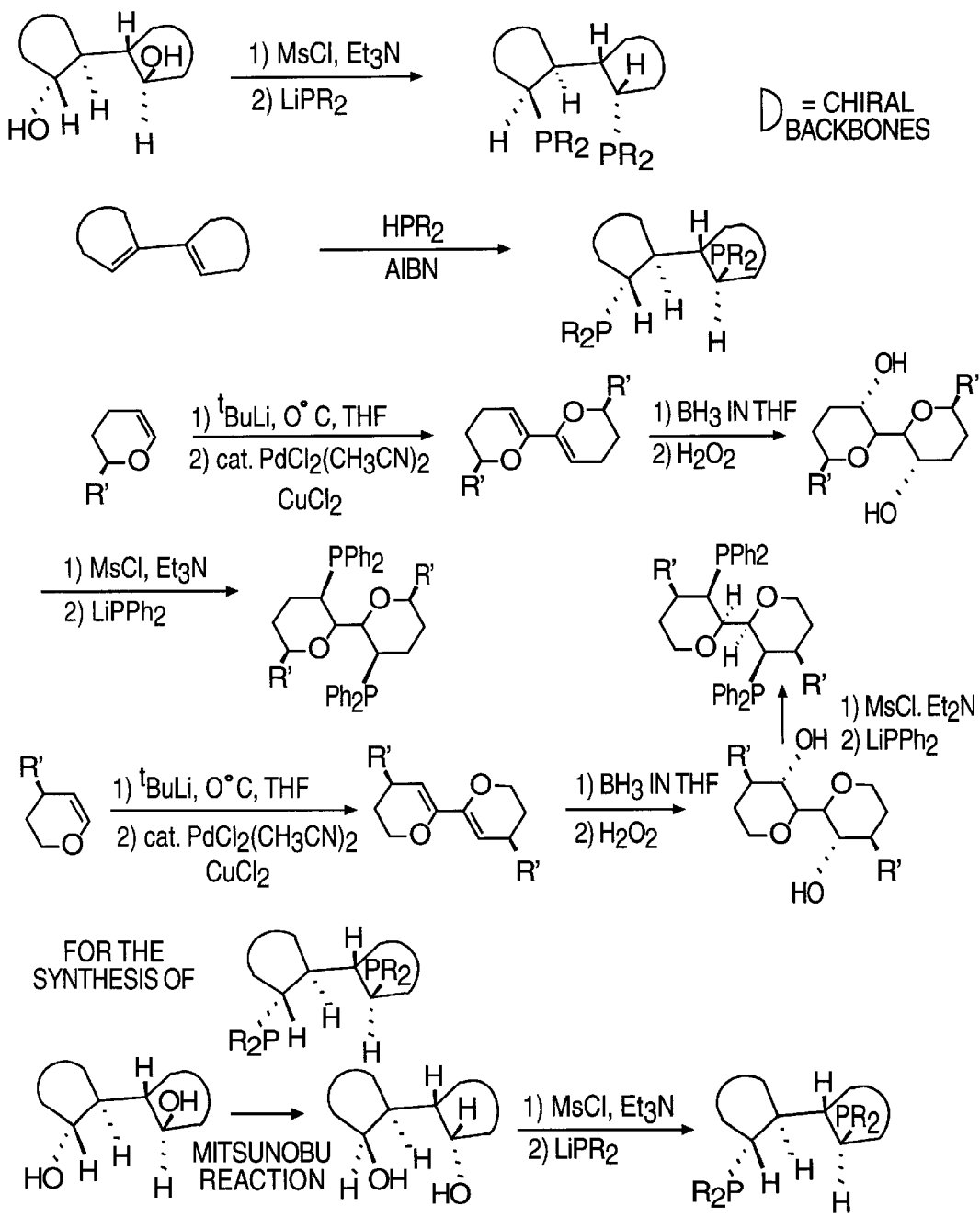
Figure 9:
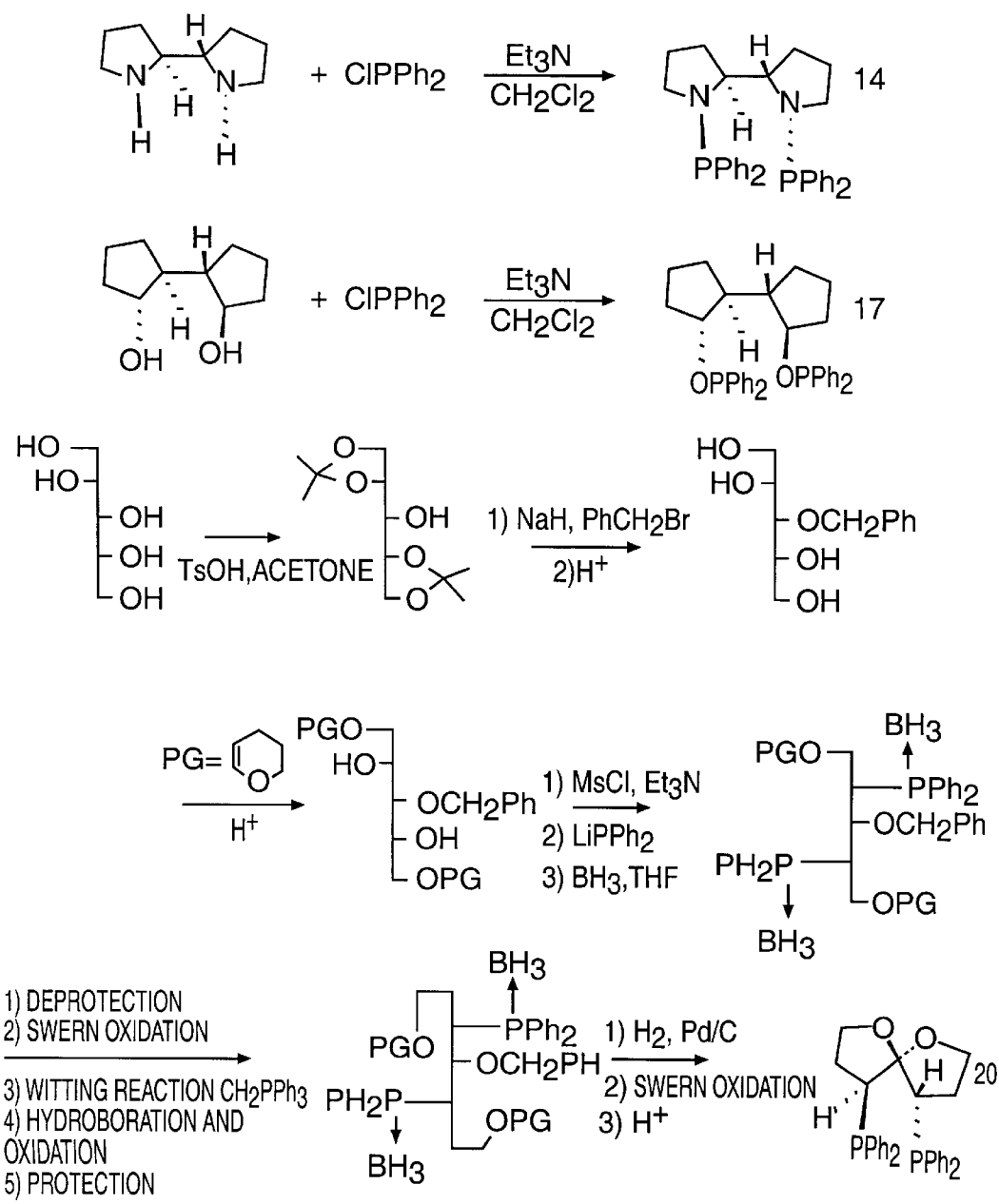
FIG. 9 illustrates the synthesis of ligands 14–23. For the chiral ligands containing P—O or P—N bonds, the corresponding chiral diols or chiral diamines are presented. For the spiro phosphines, one pathway is to construct spiro-structure in the last step. This is because direct nucleophilic attack by $LiPPh_2$ to the corresponding spiro dimesylate is difficult due to the steric hinderance of adjacent carbon group.

(as depicted in Scheme 2 and FIG. 8)

(2R,2'R)-Bis(diphenylphosphino)-(1R,1'R)-dicyclopentane (1)

To a solution of the above borane complex of the phosphine (0.24 g, 0.45 mmol) in CH$_2$Cl$_2$ (4.5 mL) was added tetrafluoroboric acid-dimethyl ether complex (0.55 mL, 4.5 mmol) dropwise via syringe at −5° C. After the addition, the reaction mixture was allowed to warm slowly to rt, and stirred for 20 h. The mixture was diluted with CH$_2$Cl$_2$, and neutralized with saturated aqueous NaHCO$_3$ solution. The aqueous layer was extracted with CH$_2$Cl$_2$. The combined organic solution was washed with brine, followed by water, and dried over Na$_2$SO$_4$. Evaporation of the solvent gave the pure phosphine. Yield: 0.21 g (93%). $^1$H NMR (CDCl$_3$, 360 MHz) δ 7.52–7.27 (m, 20 H), 2.53 (m, 2 H), 2.27 (m, 2 H), 1.93(m, 2 H), 1.72(m, 2 H), 1.70–1.43 (m, 8 H); $^{13}$C NMR (CDCl$_3$) δ 139–127 (Ph), 45.9 (d, J=12.1 Hz), 45.8 (d, J=12.0 Hz), 40.34 (d, J=14.0 Hz), 30.9 (m), 23.8 (m); $^{31}$P NMR (CDCl$_3$) δ −14.6. This phosphine was fully characterized by its borane complex.

Example 5

General Procedure for Asymmetric Hydrogenation

To a solution of [Rh(COD)$_2$]BF$_4$ (5.0 mg, 0.012 mnmol) in THF (10 mL) in a glovebox was added chiral ligand 1 (0.15 mL of 0.1 M solution in toluene, 0.015 mmol), and Et$_3$N (0.087 mL, 0.62 mmol). After stirring the mixture for 30 min, the dehydroamino acid (1.2 mmol) was added. The hydrogenation was performed at rt under 1 atm of hydrogen for 24 h. The reaction mixture was treated with CH$_2$N$_2$, then concentrated in Vacuo. The residue was passed through a short silica gel column to remove the catalyst. The enantiomeric excesses were measured by GC using a Chirasil-VAL III FSOT column. The absolute configuration of products was determined by comparing the observed rotation with the reported value. All reactions went in quantitative yield with no by-products found by GC.

Example 6

Figure 12:
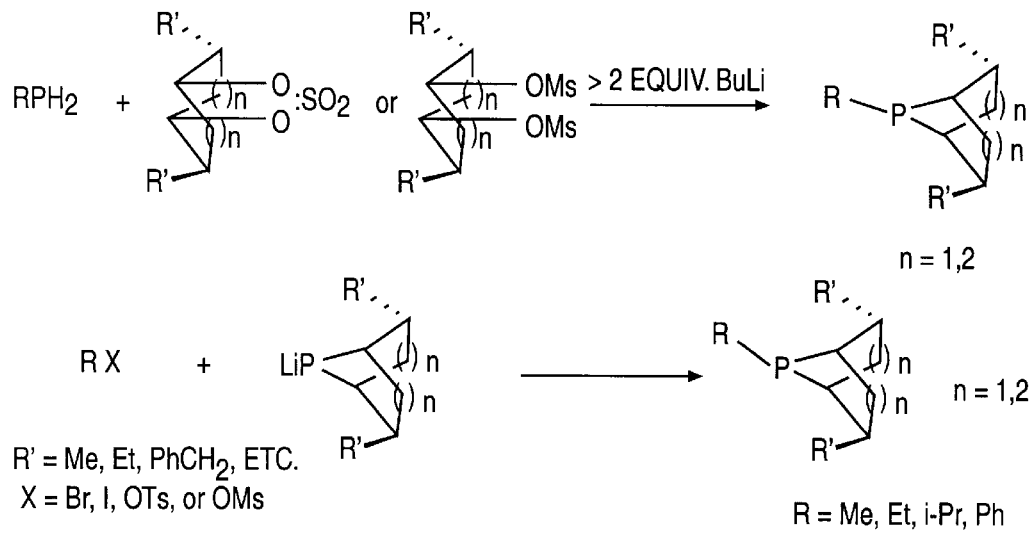
Figure 12:
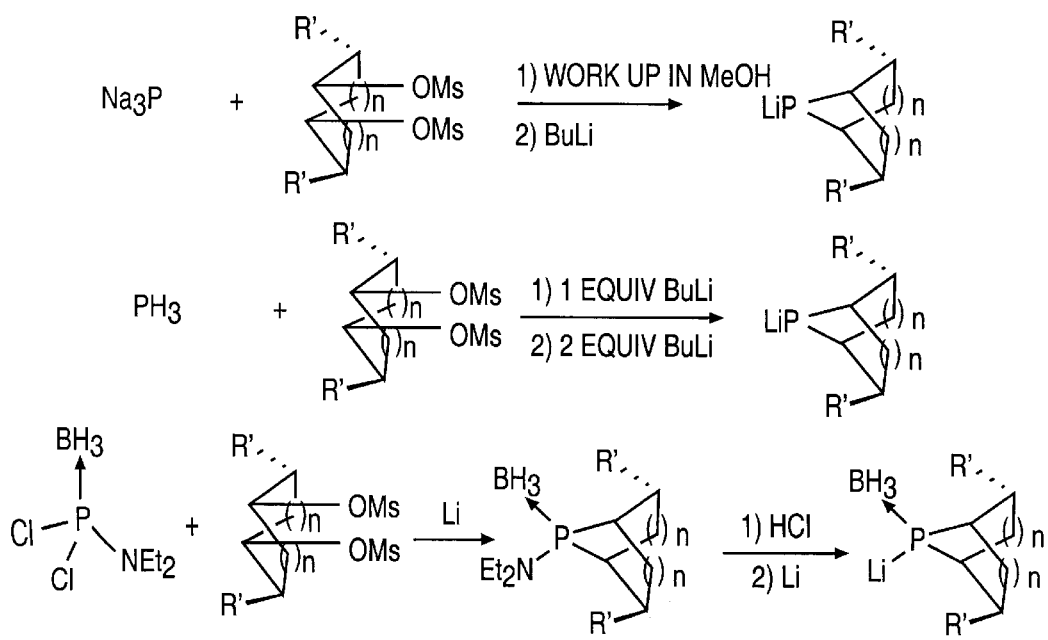
Figure 13:
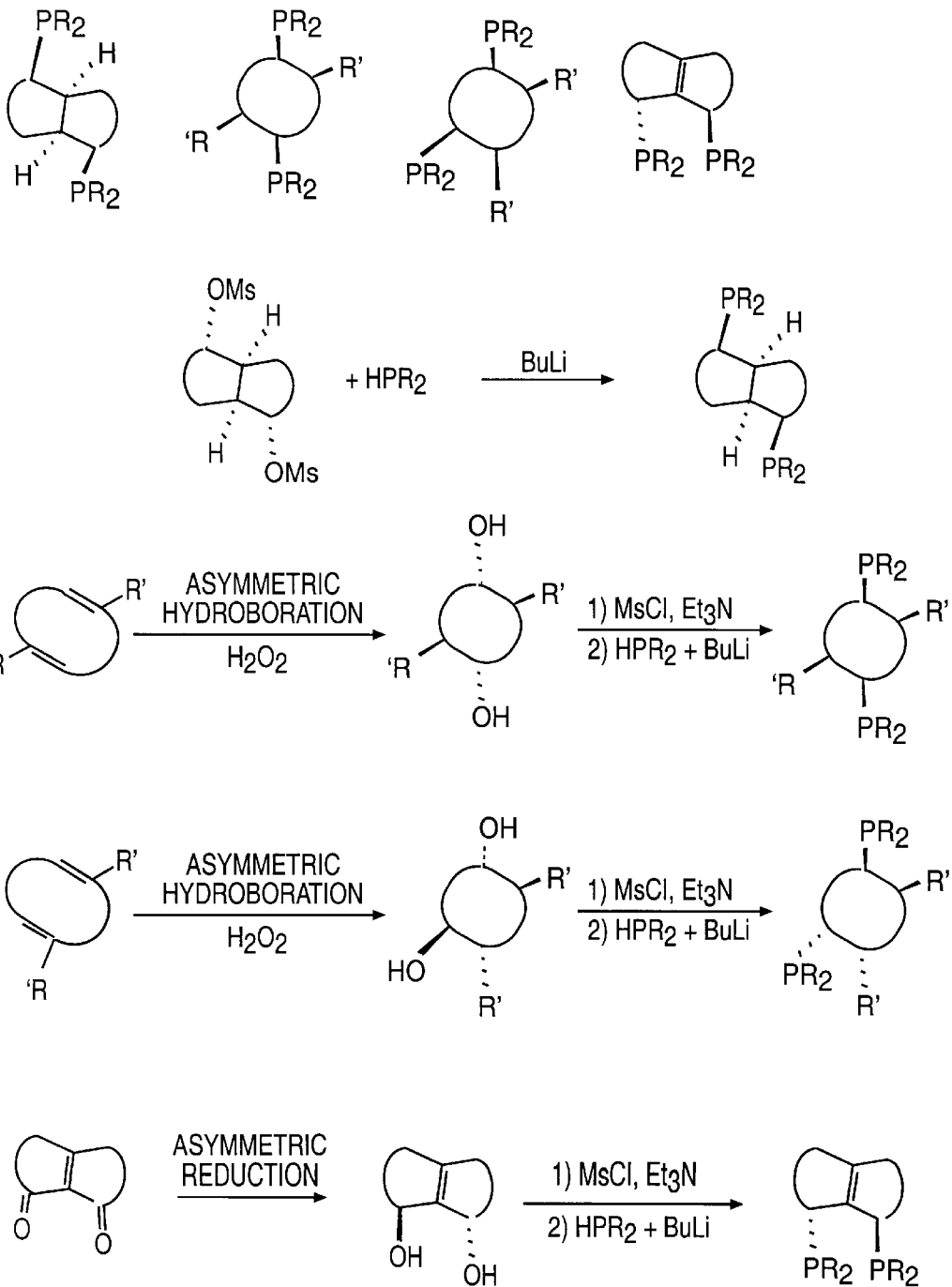
FIG. 13 outlines the synthetic procedures for ligands 45 to 50.
Figure 14:
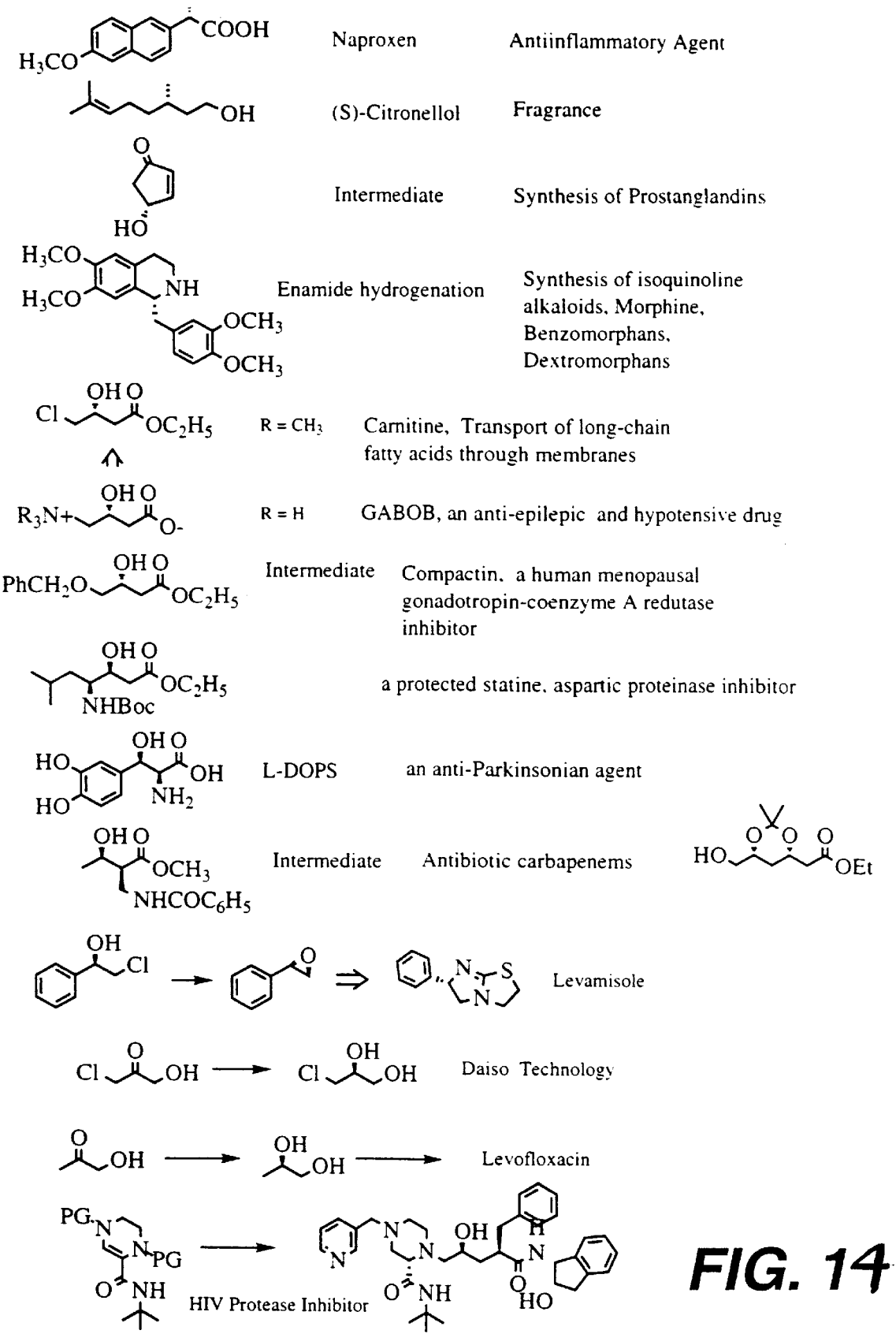
FIG. 14 illustrates applications of asymmetric catalytic reactions.

(as depicted in Scheme 5 and FIG. 12)

(1R,2S,4R,5S)-(+)-2,5-Dimethyl-7-phenyl-7-phosphabicyclo[2.2.1]heptane boraize (5)

To phenylphosphine (3.0 ml, 27.3 mmol) in TBF (200 mL) was added n-BuLi (34.5 mL of a 1.6 M solution in hexane, 55 mmol) via syringe at −78° C. over 20 min. Then the orange solution was warmed up to rt and stirred for 1 hr at rt. To the resulting orange-yellow suspension was added a solution of (1S,2S,4S,5S)-2,5-dimethylcyclohexane-1,4-diol bis(methanesulfonate) (3, 8.25 g, 27.5 mmol) in THF (100 mL) over 15 min. After the mixture was stirred overnight at rt, the pale-yellow suspension was hydrolyzed with saturated NH$_4$Cl solution. The mixture was extracted with ether (2×50 mL), and the combined organic solution was dried over anhydrous sodium sulfate. After filtration, the solvents were removed under reduced pressure. The residue was dissolved in methylene chloride (100 mL), treated with BH$_3$.THF (40 mL of a 1.0 M solution in THF, 40 mmol) and the mixture was stirred overnight. It was then poured into saturated NH$_4$Cl solution and extracted with CH$_2$Cl$_2$ (3×50 mL). The combined organic solution was dried over anhydrous Na$_2$SO$_4$ and filtered, the solvent was removed on reduced pressure. The residue was subjected to chromatography on silicon gel column, eluted with hexanes/CH$_2$Cl$_2$ (4:1) affording the product as a white solid. Yield: 1.95 g (31%). [α]$^{25}$$_D$=+59.5° (c 1.07, CHCl$_3$). $^1$H-NMR (CDCl$_3$) δ 7.60–7.30 (m, 5 H, C$_6$H$_5$), 2.60–2.40 (m, 2 H, CHP(BH$_3$)Ph), 2.15–2.05 (m, 1 H, CH), 2.04–1.80 (m, 4 H, CH$_2$), 1.65–1.50 (m, 1 H, CH), 1.32 (d, $^3$J(HH)=6.5 Hz, 3 H, CH$_3$), 0.59 (d, $^3$J(HH)=6.7 Hz, 3 H, CH$_3$), 1.6–0.2 (br, BH$_3$); $^{13}$C-NMR (CDCl$_3$) δ 131.74 (d, $^2$J(PC)=7.3 Hz, C$_{ortho}$), 130.56 (d, $^1$J(PC)=43.9 Hz, C$_{ipso}$), 129.92 (d, $^4$J(PC)=2.0 Hz, C$_{para}$), 128.44 (d, $^3$J(PC)=8.6 Hz, C$_{meta}$), 43.07 (d, $^1$J(PC)=30.5 Hz, CHP(BH$_3$)Ph), 40.85 (d, $^1$J(PC)=31.6 Hz, CHP(BH$_3$)Ph), 36.27 (CH$_2$), 36.67 (d, $^3$J(PC)=13.5 Hz, CH$_2$), 35.91 (d, $^2$J(PC)=3.5 Hz, CH), 34.65 (d, $^2$J(PC)=9.8 Hz, CH), 20.78 (CH$_3$) 20.53 (CH$_3$); $^{31}$P-NMR (CDCl$_3$) δ 36.3 (d, broad, $^1$J(PB)=58.8 Hz); HRMS Calcd for C$_{14}$H$_{22}$BP: 232.1552 (M$^+$); found: 232.1578; C$_{14}$H$_{19}$P: 218.1224 (M$^+$-BH$_3$); found: 218.1233.

Example 7

(as depicted in Scheme 5 and FIG. 12)

(1R,2R,4R,5R)-(+)-2,5-Diisopropyl-7-phenyl-7-phosphabicyclo[2.2.1]heptane borane (6)

Using the same procedure as in the preparation of 5. Yield: 0.33 g (50%). [α]$^{25}$$_D$=+25.5° (c 1.02, CHCl$_3$). $^1$H-NMR (CDCl$_3$) δ 7.55–7.30 (m, 5 H, C$_6$H$_5$), 2.85–2.70 9 (m, 2 H CHP(BH$_3$)Ph), 2.30–2.20 (m, 1 H, CH), 2.18–2.00 (m, 1 H, CH), 1.95–1.65 (m, 4 H, CH$_2$), 1.40–1.20 (m, 2 H, CH), 1.03 (d, $^3$J(PH)=6.5 Hz, CH$_3$), 0.87 (d, $^3$J(PH)=6.7 Hz, CH$_3$), 0.85 (d, $^3$J(PH)=7.4 Hz, CH$_3$), 0.53 (s, broad, 3 H, CH$_3$), 1.5–0.2 (broad, BH$_3$); $^{13}$C-NMR (CDCl$_3$) δ 131.19 (d, $^2$J(PC)=8.3 Hz, C$_{ortho}$), 130.71 (d, $^1$J(PC)=45.2 Hz, C$_{ipso}$), 129.97 (d, $^4$J(PC)=2.5 Hz, C$_{para}$), 128.45 (d, $^3$J(PC)=9.5 Hz, C$_{meta}$), 50.30 (d, $^2$J(PC)=2.1 Hz, CH), 48.77 (d, $^2$J(PC)=9.7 Hz, CH), 38.27 (d, $^1$J(PC)=30.5 Hz, CHP(BH$_3$)Ph), 36.81 (CH$_2$), 36.71 (d, $^1$J(PC)=31.5 Hz, CHP(BH$_3$)Ph), 34.73 (d, $^3$J(PC)=13.7 Hz, CH$_2$), 31.92 (CHMe$_2$), 31.12 (CHMe$_2$), 22.41 (CH$_3$), 21.55 (CH$_3$), 20.73 (CH$_3$), 20.10 (CH$_3$); $^{31}$P-NMR (CDCl$_3$) δ 36.d (d, broad, $^1$J(PB)=51.4 Hz).

Example 8

(as depicted in Scheme 5 and FIG. 12)

(1R,2S, 4R,5S)-(+)-2,5-Dimethyl-7-phenyl-7-phosphabicyclo[2.2.1]heptane (40)

To a solution of corresponding borane complex of the phosphine (5, 1.0 g, 4.31 mmol) in CH$_2$Cl$_2$ (22 mL) was added tetrafluoroboric acid-dimethyl ether complex (2.63 mL, 21.6 mmol) dropwise via a syringe at −5° C. After the addition, the reaction mixture was allowed to warm up slowly, and stirred at rt. After 20 h, $^{31}$P NMR showed the reaction was over, it was diluted by $CH_2Cl_2$, neutralized by saturated $NaHCO_3$ aqueous solution. The aqueous layer was extracted with $CH_2Cl_2$. The combined organic solution was washed with brine, followed by water, and then dried over $Na_2SO_4$. Evaporation of the solvent gave a pure phosphine product, which was confirmed by NMR. Yield: 0.9 g (96%). $[\alpha]^{25}{}_D$=+92.5° (c 2.3, toluene); $^1$H NMR (CDCl$_3$, 360 MHz) δ 7.38–7.34 (m, 2H), 7.26–7.21 (m, 2H), 7.19–7.16 (m, 1H), 2.60–2.54 (m, 2H), 1.89–1.62 (m, 5H), 1.44–1.42 (m, 1H), 1.16 (d, J=6.12 Hz, 3H), 0.55 (d, J=6.95 Hz, 3H); $^{13}$C NMR (CDCl$_3$) δ 138.68 (d, J=29.3 Hz), 131.42 (d, J=13.0 Hz), 127.88 (d, J=2.35 Hz), 126.57 (s), 47.34 (d, J=13.5 Hz), 45.26 (d, J=10.2 Hz), 39.21 (d, J=6.7 Hz), 39.21 (d, J=5.3 Hz), 38.74 (d, J=6.7 Hz), 34.69 (d, 17.2 Hz), 22.37 (d, J=7.8 Hz), 21.52 (s); $^{31}$P NMR(CDCl$_3$) δ −7.29.

Example 9

(as depicted in Scheme 5 and FIG. 12)

(1R,2R,4R,5R)-(+)-2,5-Diisopropyl-7-phenyl-7-phosphabicyclo[2.2.1]heptane (8 in scheme 5)

Using the same procedure as in the preparation of 7. Yield: 1.0 g (95.5%). $[\alpha]^{25}{}_{D=+}$43.9° (c 1.2, toluene); $^1$H NMR (CDCl$_3$, 360 MHz) δ 7.35–7.30 (m, 2H), 7.24–7.14 (m, 3H), 2.94–2.85 (m, 2H), 1.76–1.53 (m, 5H), 1.25–1.14 (m, 2H), 1.06 (d, J=7.77 Hz, 3H), 0.95–08.0 (m, 1H), 0.87 (dd, J=3.77 Hz, 7.89 Hz, 6 H), 0.49 (d, J=9.30 Hz, 3H); $^{13}$C NMR (CDCl$_3$) δ 138.83 (d, J=30.49 Hz), 130.69 (d, J=12.2 Hz), 127.71 (d, J=2.87 Hz), 126.45 (s), 53.38 (d, J=6.34 Hz), 48.63 (d, J=17.06 Hz), 41.97 (d, J=13.4 Hz), 40.51 (d, J=9.96 Hz), 37.60 (d, J=11.09 Hz), 37.39 (d, J=9.74 Hz), 33.03 (d, 6.11 Hz), 31.86 (s), 21.89 (s), 21.78 (s), 21.23 (s), 20.40 (s); $^{31}$P NMR(CDCl$_3$) δ −7.49.

Example 10

Enantioselective Allylic Alkylation

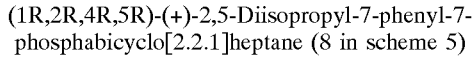

The procedures are exemplified by the experiments carried out with ligand 7 in toluene. To a stirring solution of $[Pd_2(\eta^3\text{-}C_3H_5)_2Cl_2]$ (3.0 mg, 0.008 mmol) in toluene (1.5 mL) was added ligand 7 (0.36 mL of 0.1 M solution in toluene, 0.036 mmol) under a nitrogen atmosphere. After 30 mins, racemic 1,3-diphenyl-1-acetoxypropene (150 mg, 0.60 mmol) was added. Then the solution was allowed to be stirred 30 mins. N,O-bis(trimethylsiyl)acetamide (0.44 mL, 1.8 mmol), dimethyl malonate (0.21 mL, 1.8 mmol) and potassium acetate (3 mg, 0.03 mmol) were added in this order. The reaction was monitored by TLC (eluent: Hexane/ethyl acetate=10/1). After 1.5 hrs, TLC showed the reaction was over. After the solvent was evaporated in vacuo, column chromatography on silica gel (eluent: Hexane/ethyl acetate=10/1) of the residue yielded the pure product: Yield: 190 mg, 97.7%. The optical purity was determined to be 95.5% ee by BPLC (Daicel Chiralcel OD column, 1 ml/min, hexane/2-propanol=99/1).

Example 11

Typical Procedure for Hydrogenation of Imines

To a solution of chloro(1,5cyclooctadiene)iridium(I) dimer (2 mg, 0.003 mmol) in toluene (4 mL) was added a solution of BICP in toluene (0.1 M, 71 ul, 0.0071 mmol), the resulting solution was stirred in glovebox for 30 min. Then phthalimide (3.5 mg, mmol) was added and the reaction mixture was stirred for another 30 min before 2,3,3-trimethylindolenine (96 ul, 0.6 mmol) was added. The reaction tube was placed in an autoclave, pressurized with hydrogen to 1000 psi after several exchange with hydrogen, and stirred at rt for 65 h. Conversion (97.8%) and enantiomeric excess (92.2%) were determined by GC (a capillary column: γ-dex-225).

Example 12

Figure 11:
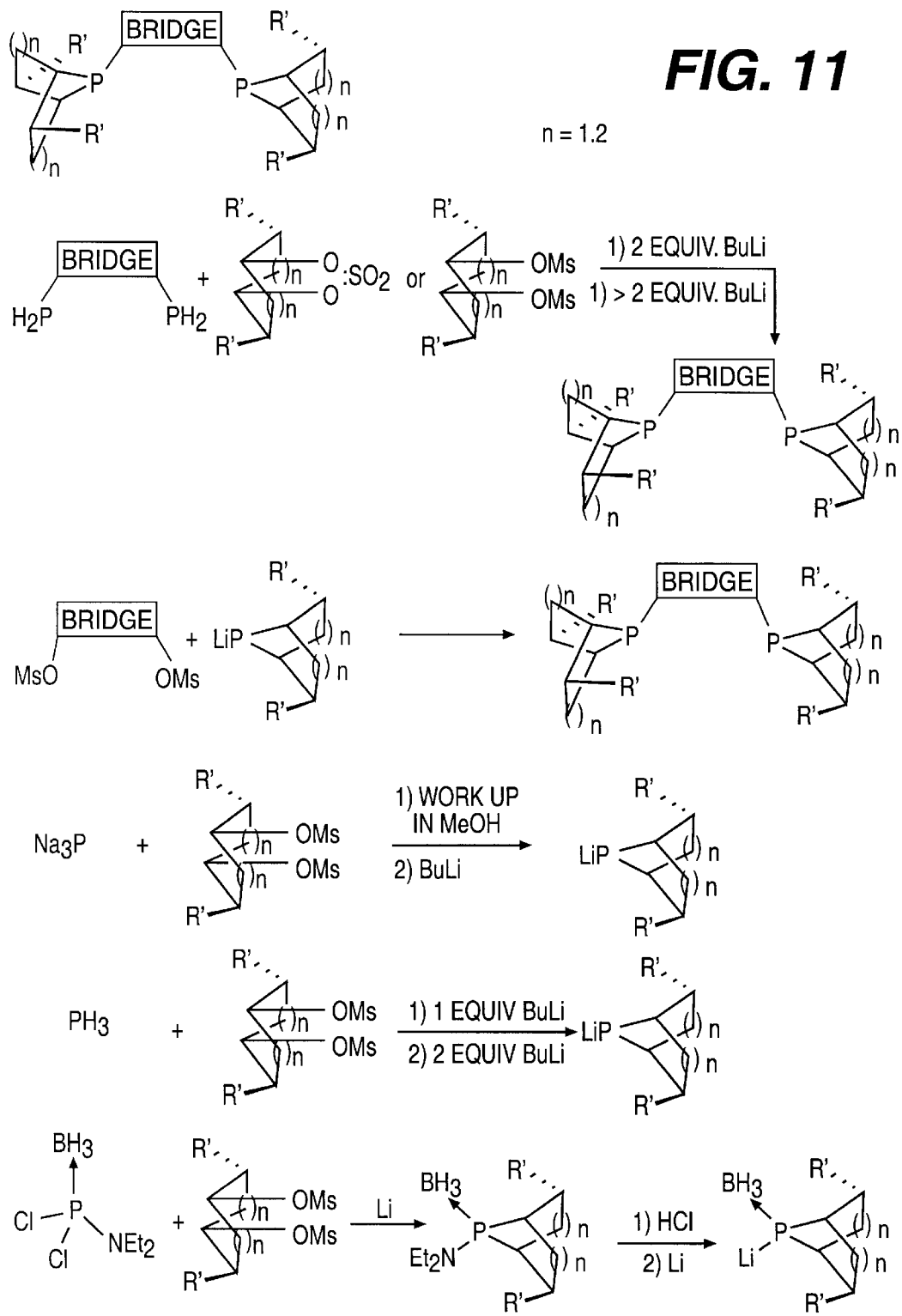
FIGS. 11 and 12 describe the synthesis of chiral fused phospha-bicyclic compounds. A typical procedure uses $RPLi_2$ as nucleophiles. However, phospha-bicyclic anion can be made and nucleophilic attack with bridge groups (XRX or RX where R is alkyl or aryl and X is a halide, tosylate or mesylate) by this anion can generate the desired ligands.

(as depicted in Scheme 3, FIG. 5 and FIG. 11)

Me-PennPhos: 1,2-Bis{(1R,2S,4R,5S)-2,5-dihethyl-8-phenylphospha-bicyclo[2.2.1]heptyl}benzene (36a)

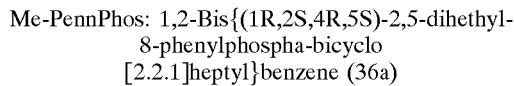

To the suspension of NaH (8.0 g, 333 mmol) in THF (200 ml), cooled to 0° C., was added 1,2-diphosphinobenzene (4.0 ml, 30.4 mmol), followed by HMPA (80 ml). The resulting orange suspension was stirred at 0° C. for 1 h. (1S,2S,4S,5S)-2,5-dimethylcyclohexane-1,4-diol dimesolate (18.3 g, 60.9 mmol) in THF (150 ml) was added over 20 min. The resulting orange-red suspension was stirred at RT for 3.5 days, hydrolyzed with NaCl-H$_2$O and then extracted with hexane (2×100 ml). The combined organic solution was dried over Na$_2$SO$_4$. After filtration, the solvents were removed under reduced pressure. The residue was subjected to chromatography on silica gel column, eluted with hexane. Yield: 3.0 g (27.5%). $^1$H-NMR (CDCl$_3$): δ H=7.25–7.10 (m, 2 H, aromatic), 7.08–6.95 (m, 2 H, aromatic), 3.21 (d, broad, 2 H, $^2$J(PH)=14.5 Hz, PCH), 2.58 (d, broad, 2 H, $^2$J(PH)= 13.4 Hz, PCH), 1.90–1.60 (m, 12 H), 1.55–1.35 (m, 2 H,), 1.17 (d, 6 H, $^3$J(HH)=6.3 Hz, CH$_3$), 0.60 (d, 6 H, $^3$J(HH)=6.3 Hz, CH$_3$). CH. $^{13}$C-NMR (is out of first order, CDCl$_3$): δ C=143.94, 143.66, 143.48, 143.20, 131.05, 131.00, 130.93, 126.33, 46,24, 46.20, 46,17, 46.13, 45.92, 45.69, 45.61, 45.38, 40.17, 40.05, 39.89, 39.73, 39.61, 39.52, 39.33, 39.29, 39.26, 34.76, 34.61, 34.51, 34.41, 34.26, 22.69, 22.65, 22.61, 20.82. $^{31}$P-NMR (CDCl$_3$): δ P=−7.3 ppm.

Example 13

(as depicted in Scheme 3 and FIG. 11)

i-Pr-PennPhos: 1,2-Bis{(1R,2R,4R,5R)-2,5-bis-isopropyl-8-phenylphos-phabicyclo[2.2.1]heptyl}benzene (36b)

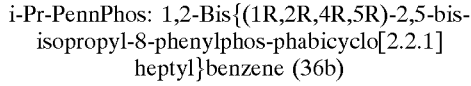

1,2-diphosphinobenzene (0.4 ml, 3.04 mmol) and NaH (0.9 g, 37.5 mmol) were mixed in THF (50 ml) and cooled to 0° C. HMPA (8.5 ml, 49 mmol) was added. The resulting orange suspension was stirred at 0° C. for 1 h and then (1S,2S,4S,5S)-2,5-dimethyl-cyclohexane-1,4-diol dimesolate (2.17 g, 6.08 mmol) in THF (40 ml) was added over 10 min. The resulting orange-red suspension was stirred at RT for 3 days. After cooled to 0° C., it was hydrolyzed with NaCl-H$_2$O, and extracted with hexane (2×50 ml). The combined organic solution was dried over Na$_2$SO$_4$ and filtered. The solvents were removed under reduced pressure. The residue was subjected to chromatography on silica gel column, eluted with hexane. Yield: 0.6 g (42%). $^1$H-NMR (CDCl$_3$): δ H=7.20–7.10 (m, 2 H, aromatic), 7.05–6.90 (m, 2 H, aromatic), 3.38 (d, broad, 2 H, $^2$J(PH)=14.2 Hz, PCH), 2.85 (d, broad, 2 H, $^2$J(PH)=13.5 Hz, PCH), 1.85–1.45 (m, 12 H), 1.30–1.08 (m, 4 H), 1.03 (d, 6H, $^3$J(HH)=6.4 Hz, CH$_3$), 0.96 (d, 6H, $^3$J(HH)=5.6 Hz, CH$_3$), 0.86 (d, 6H, $^3$J(HH)=6.5 Hz, CH$_3$), 0.47 (s, 6 H, CH$_3$). $^{13}$C-NMR (is out of first order, CDCl$_3$): δ C=143.97, 143.62, 143.56, 143.50, 143.45, 143.09, 130.96, 130.90, 130.86, 126.11, 54.10, 54.06, 54.03, 48.65, 48.56, 48.46, 42.02, 41.96, 41.24, 41.20, 41.18, 41.14, 37.94, 37.77, 37.60, 37.46, 33.29, 33.27, 33.24, 31.69, 23.45, 23.40, 23.35, 22.22, 20.97, 20.54, $^{31}$P-NMR (CDCl$_3$): δ P=−8.7 ppm.

Example 14

Figure 10:
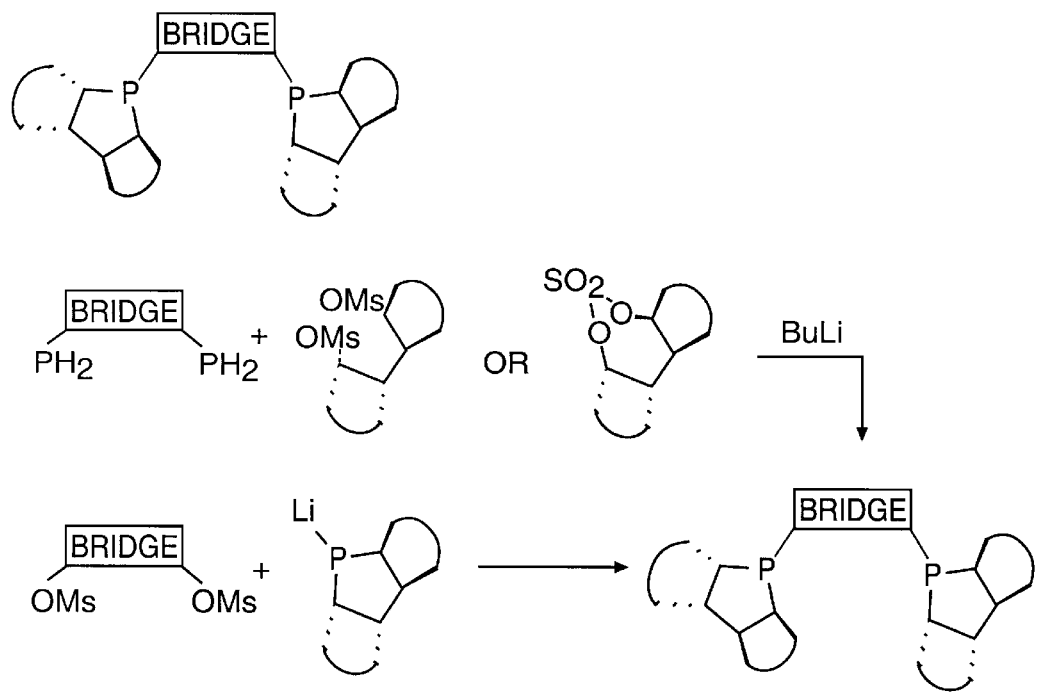
FIG. 10 describes the synthesis of phospha-tricyclic compounds from the corresponding diols.
Figure 10:
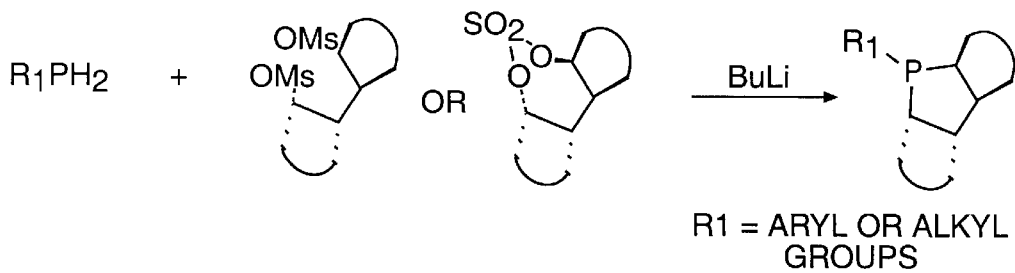

(as depicted in Scheme 4, FIG. 4 and FIG. 10)

C5-Tricyclophos: 1,2-Bis{(2R,6R,7R,11R) phosphatricyclo[3.3.0.0]undecanyl}-benzene (26)

1,2-diphosphinobenzene (0.20 ml, 1.52 mmol) and NaH (0.40 g, 16.7 mmol) were mixed in THF (50 ml) and cooled to 0° C. HMPA (4.3 ml, 25 mmol) was added. The resulting orange suspension was stirred at 0° C. for 1 h and then treated with (1R,1'R,2S,2'S)-1,1'-bicyclopentyl-2,2'-diol bismesylate (0.993 g, 3.04 mmol) in THF (40 ml). The resulting orange-red suspension was stirred at RT for 20 h, pale orange-yellow suspension formed. After cooled to 0° C., it was hydrolyzed with NaCl-H$_2$O, and extracted with hexane (2×50 ml). The combined organic solution was dried over Na$_2$SO$_4$ and filtered. The solvents were removed under reduced pressure. The residue was subjected to chromatography on silica gel column, eluted with hexaneether (40:1.5). Yield: 0.42 g (67%). $^1$H-NMR (CDCl$_3$): δ H=7.50–7.30 (m, 2 H, aromatic), 7.25–7.10 (m, 2 H, aromatic), 3.15–2.95 (m, 2 H, PCH), 2.85–2.70 (m, 2 H, PCH), 2.50–2.30 (m, 4 H, CH), 2.05–1.00 (m, 24 H, CH$_2$). $^{13}$C-NMR (is out of first order, CDCl$_3$): δ C=144.03, 143.98, 130.16, 130.12, 130.08, 127.50, 53.64, 52.97, 44.72, 44.66, 44.60, 43.07, 32.64, 32.01, 31.86, 31.68, 30.58, 26.47, 25.41, 25.36, 25.31. $^{31}$P-NMR (CDCl$_3$): δ P=9.6 ppm.

Example 15

General Procedure for Asymmetric Hydrogenation of Dehydroaminoacids for Pennphos ligands In a glovebox, a schlenk reaction bottle was charged with a given amount of Rh catalyst precursor and Me-PennPhos in a ratio of 1.1 mol ligand per 1 mol Rh and 10 ml of the given solvent (dried and degassed), the resulting orange-yellow solution was stirred at rt for 20 min. Then substrate (1 mmol, sub/cat=100) was added. The nitrogen atmosphere was exchanged to H$_2$ by flashing the schlenk with H$_2$. The reaction mixture was then stirred at RT and 1 atm H$_2$ for a certain period of time. The reaction solution was passed through a short silica gel, washed with ether. The conversion and ee were measured by GC analysis on Chirasil-Val III column. The absolute configuration was determined by measuring the rotation of product and comparing with the corresponding standard values.

Example 16

General Procedure for Asymmetric Hydrogenation of Ketontes

In a glovebox, a reaction bottle was charged with [Rh(COD)Cl]$_2$ (2.5 mg, 0.0101 mmol) and Me-PennPhos (3.7 mg, 0.0103 mmol), and MeOH (10 ml, dried and degassed), the resulting orange-yellow solution was stirred at rt for 30 min. Then ketone substrate (1 mmol, substrate/catalyst=100) was added. The reaction solution was then placed in an autoclave. The nitrogen atmosphere was exchanged to H$_2$ by flashing the autoclave with H$_2$ (10 to 20 atm). The autoclave was pressurized to a certain atmosphere of H$_2$. The reaction mixture was then stirred at RT for a given period of time. The reaction solution was then passed through a short silica gel, washed with ether. The conversion and ee were measured by GC analysis on chiral β-dex 120 column. The absolute configuration was determined by measuring the rotation of product and comparing with the corresponding standard values.

Example 17

General Procedure for Asymmetric Hydrogenation of beta-Keto esters

BICP (0.01 mol) and Ru(COD)(2-methylallyl)$_2$ (0.01 mol) were placed in a 10 ml Schlenk tube and the vessel was purged with argon. 2 mL of anhydrous acetone were added. To this suspension was added methanolic HBr (0.11 ml of a 0.29 M solution) and the suspension was stirred 30 min at rt. The solvent was thoroughly evaporated under vacuum and the Ru(BICP)Br$_2$ obtained was used immediately. The solution of appropriate substrate (1 mmol) in degassed solvent (2 ml) was placed in a 10 ml Schlenck tube and degasses by 3 cycles of vacuum/argon. This mixture was added to the catalyst (1%) in a glass vessel and placed under argon in 300 ml stainless steel autoclave. The Argon atmosphere was replaced with hydrogen. The hydrogenations were run under the reaction conditions given The solvent was removed under pressure. Conversion and ee are determined by chiral GC column β-dex 120 and γ-dex 225.

The above examples illustrate the present invention and are not intended to limit the invention in spirit or scope.

REFERENCES 1. (a) Morrison, J. D., Ed. *Asymmetric Synthesis* Academic Press: New York, 1985, Vol. 5. (b) Bosnich, B., Ed. *Asymmetric Catalysis* Martinus Nijhoff Publishers: Dordrecht, The Netherlands, 1986. (c) Brunner, H. *Synthesis* 1988, 645. (d) Noyori, R.; Kitamura, M. In *Modern Synthetic Methods*; Scheffold, R., Ed.; Springer-Verlag: Berlin Hedelberg, 1989, Vol. 5, p 115. (f) Nugent, W. A., RajanBabu, T. V., Burk, M. J. *Science* 1993, 259, 479. (g) Ojima, I., Ed. *Catalytic Asymmetric Synthesis*, VCH: New York, 1993. (h) Noyori, R. *Asymmetric Catalysis In Organic Synthesis*, John Wiley & Sons, Inc: New York, 1994.
2. (a) Brunner, H. In *Topics in Stereochemistry*; Interscience: New York, 1988, Vol. 18, p129. (b) Brunner, H.; Zetlmeier W., Eds. *Handbook of Enantioselective Catalysis*, VCH: New York, 1993, Vol. 2.
3. (a) Knowles, W. S.; Sabacky, M. J.; Vineyard, B. D. *J. Chem. Soc., Chem. Commun.* 1972, 10. (b) Vineyard, B. D.; Knowles, W. S.; Sabacky, M. J.; Bachman, G. L.; Weinkauff, D. J. *J. Am. Chem. Soc.* 1977, 99, 5946.
4. (a) Achiwa, K. *J. Am. Chem. Soc.* 1976, 98, 8265. (b) Ojima, I.; Yoda, N. *Tetrahedron Lett.* 1980, 21, 7865.
5. Nagel, U.; Kinzel, E.; Andrade, J.; Prescher, G. *Chem. Ber.* 1986, 119, 3326.
6. Kagan, H. B.; Dang, T.-P. *J. Am. Chem. Soc.* 1972, 94, 6429.
7. Fryzuk, M. D.; Bosnich, B. *J. Am. Chem. Soc.* 1977, 99, 6262.
8. MacNeil, P. A.; Roberts, N. K.; Bosnich, B. *J. Am. Chem. Soc.* 1981, 103, 2273.
9. (a) Miyashita, A.; Yasuda, A.; Takaya, H.; Toriumi, K.; Ito, T.; Souchi, T.; Noyori, R. *J. Am. Chem. Soc.* 1980, 102, 7932. (b) Miyashita, A.; Takaya, H.; Souchi, T.; Noyori, R. *Tetrahedron* 1984, 40, 1245. (c) Takaya, H.; Mashima, K.; Koyano, K.; Yagi, M.; Kumobayashi, H.; Takemomi, T.; Akugawa, S.; Noyori, R. *J. Org. Chem.* 1986, 51, 629. (d) Takaya, H.; Akutagawa, S.; Noyori, R. *Org. Synth.* 1988, 67, 20.

10. (a) Burk, M. J.; Feaster, J. E.; Harlow, R. L. *Organometallics* 1990, 9, 2653. (b) Burk, M. J. *J. Am. Chem. Soc.* 1991, 113, 8518.

11. (a) Corey, E. J. Danheiser, R. L.; Chandrasekaran, S. *J. Org. Chem.* 1976, 41, 260. (b) Greidinger, D. S.; Ginsburg, D. *J. Org. Chem.* 1957, 22, 1406.

12. Brown, H. C.; Jadhav, P. K.; Mandal, A. K. *J. Org. Chem.* 1982, 47, 5074.

13. Chen, Z.; Eriks, K.; Halterman, R. L. *Organiometallics* 1991, 10, 3449.

14. Halternan, R. L.; Vollhardt, K. P. C.; Welker, M. E.; Blaser, D.; Boese, R. *J. Am. Chem. Soc.* 1987, 109, 8105.

15. Reviews: (a) Trost, B. M.; Van Vranken, D. L. *Chem. Rev.* 1996, 96, 395. (b) Hayashi. T. In *Catalytic Asymmetric Synthesis*; Ojima, I. Ed; VCH Publishers: New York, 1993; 325. (c) Consiglio, G.; Waymouth, R. M. *Chem. Rev.* 1989, 89, 257.

What is claimed is:

1. A conformationally rigid chiral phosphine ligand, wherein said ligand comprises a 2,2'-bis(diorganophosphino)-1,1'-bis(cyclic) structure, wherein each cycle of the bis(cyclic) structure comprises three to eight carbon atoms, and wherein the 1, 1', 2, and 2' carbon atoms in said structure are saturated.

2. A ligand according to claim 1, wherein said ring is substituted with alkyl or aryl groups.

3. The ligand of claim 1, wherein said ring is substituted with a fused aryl or alkyl substituent.

4. A ligand according to claim 1, selected from the compounds of the following formulas and the corresponding enantiomers

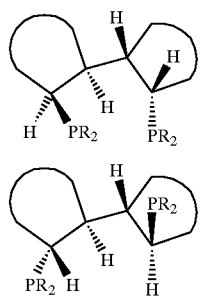

wherein each variable ring contains three to eight carbon atoms, wherein said ring may be unsubstituted or substituted with alkyl or aryl groups, and wherein R is substituted or unsubstituted aryl or substituted or unsubstituted alkyl.

5. The chiral phosphine ligand of claim 1 wherein each of the 1, 1', 2, and 2' saturated carbon atoms is a chiral center.

6. The chiral phosphine ligand of claim 1 wherein the ligand is capable of forming a seven membered ring with a transition metal.

7. A chiral phosphine ligand according to claim 4, selected from the compounds of the following formulas and the corresponding enantiomers:

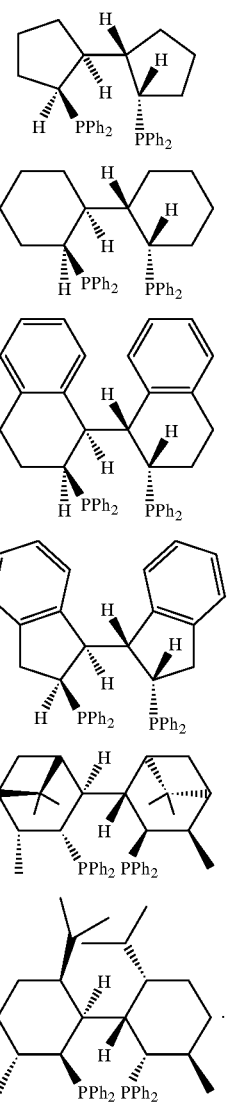

8. A chiral phosphine ligand according to claim 4, selected from a compound of the following formula and the corresponding enantiomer:

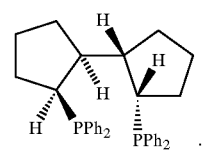

9. A conformationally rigid chiral bis(phospholane) ligand, selected from a compound of the following formula and the corresponding enantiomer:

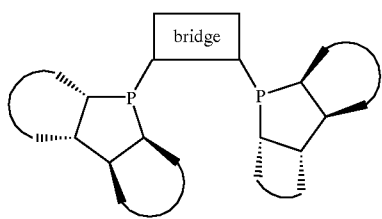

wherein each variable ring contains three to eight carbon atoms, wherein said ring may be unsubstituted or substituted with alkyl or aryl groups, and wherein the bridge is a diradical.

10. The ligand of claim 9, wherein the bridge is an alkyl or aryl diradical.

11. The ligand of claim 9, wherein the bridge is selected from the group consisting of —(CH$_2$)$_r$—, —(CH$_2$)$_s$Z(CH$_2$)$_m$—, 1,2-divalent phenyl, 2,2'-divalent 1,1'-biphenyl, and 2,2'-divalent 1,2'-binaphthyl; wherein r, s and m are the same or different integers from 1 to 8 and Z is selected from the group consisting of O, S, NR", PR", wherein R" is alkyl or aryl.

12. A ligand according to claim 9, wherein each variable ring contains 5 carbon atoms.

13. A ligand according to claim 9, wherein each variable ring contains a fused aryl substituent.

14. A chiral phosphine ligand according to claim 10, selected from a compound of the following formula and the corresponding enantiomer:

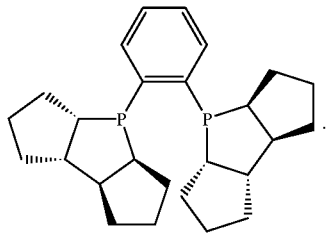

15. A chiral phosphine ligand selected from a compound of the following formula and the corresponding enantiomer:

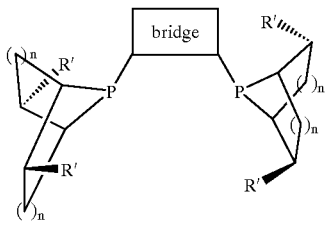

wherein the bridge is a diradical, R' is substituted or unsubstituted alkyl or substituted or unsubstituted aryl, and n is 1 or 2.

16. A ligand according to claim 15, wherein said bridge is alkyl or aryl diradical.

17. A ligand according to claim 15, wherein said bridge is selected from the group consisting of —(CH$_2$)$_r$—, —(CH$_2$)$_s$Z(CH$_2$)$_m$—, 1,2 divalent phenyl, 2,'2 divalent 1,1' biphenyl, and 2,2' divalent 1,2' binaphthyl; wherein r, s and m are the same or different integers from 1 to 8 and Z is selected from the group consisting of O, S, NR", PR", wherein R" is alkyl or aryl.

18. A chiral phosphine ligand according to claim 15 selected from the compounds of the following formulas and the corresponding enantiomers:

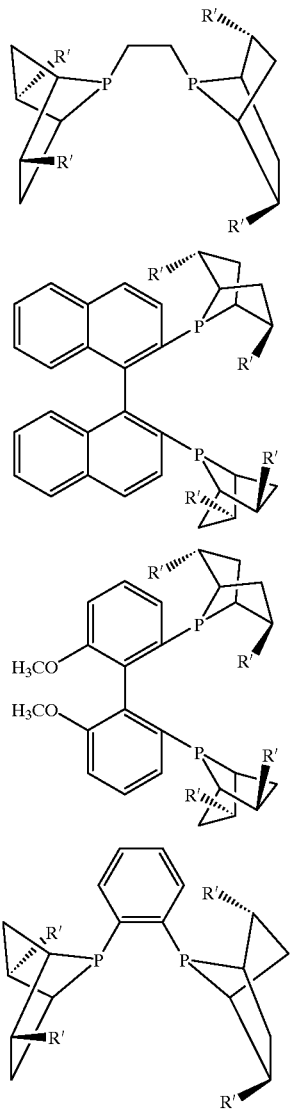

wherein R' is substituted or unsubstituted alkyl or substituted or unsubstituted aryl.

19. A chiral phosphine ligand according to claim 15, selected from a compound of the following formula and the corresponding enantiomer:

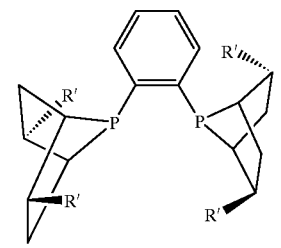

wherein each R' is substituted or unsubstituted alkyl, or substituted or unsubstituted aryl.

20. A bidentate bis(diorganophosphino) structure selected from a compound of the following formula and the corresponding enantiomer:

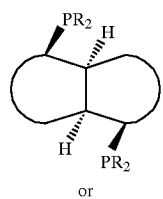

or

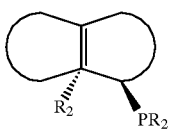

wherein each variable ring contains three to eight carbon atoms, and wherein R is substituted or unsubstituted aryl, or substituted or unsubstitdted alkyl.

21. A chiral phosphine ligand according to claim 20 having the following structure or that of the corresponding enantiomer:

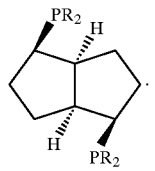

22. A rigid bidentate chiral phosphine ligand having a monocyclic, structure of 4 to 20 carbon atoms, wherein the monocyclic structure comprises two vicinally substituted pairs of carbon atoms wherein a first carbon atom of each pair of carbon atoms is bonded to a phosphine group and a second carbon atom of each pair of carbon atoms is bonded to a substituted or unsubstituted alkyl or aryl, and wherein said alkyl or aryl groups are in cis or trans orientation with respect to the monocyclic structure.

23. A chiral phosphine ligand, according to claim 22, selected from the compounds of the following formulas and the corresponding enantiomers:

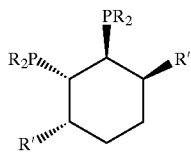

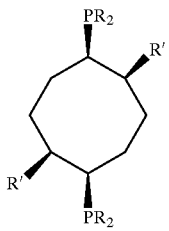

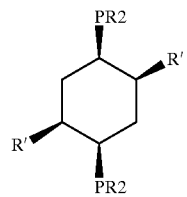

wherein R' is substituted or unsubstituted alkyl or substituted or unsubstituted aryl, and R is substituted or unsubstituted alkyl or substituted or unsubstituted aryl.

24. A monodentate chiral phospholane ligand, wherein said ligand comprises the compounds of the following formulas and the corresponding enantiomers:

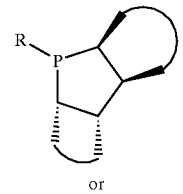

or

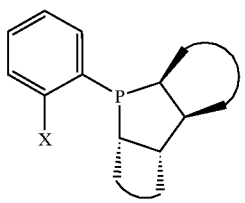

wherein each variable ring contains three to eight carbon atoms, R is substituted or unsubstituted aryl or alkyl, and X is selected from the group consisting of chiral oxazolines, COOH, OMe, OH, SMe, SH, amines and diphenylphosphine.

25. A monodentate chiral phospholane ligand according to claim 24, selected from a compound of the following formula and the corresponding enantiomer:

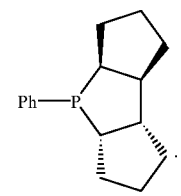

26. A monodentate chiral phosphine ligand selected from a compound of the following formula and the corresponding enantiomer:

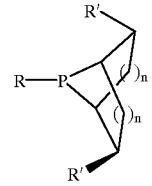

wherein R and R' are independently selected from substituted or unsubstituted aryl or substituted or unsubstituted alkyl and wherein n is 1 or 2.

27. A monodentate chiral phosphine ligand according to claim 26 wherein the monodentate chiral phosphine ligand is a compound of the following formula and the corresponding enantiomer:

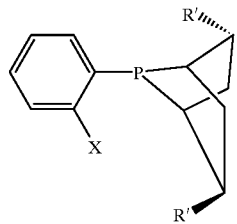

wherein n is 1, X is selected from the group consisting of chiral oxazolines, COOH, OMe, OH, H, SMe, SH PPh$_2$ and amines, and R' is substituted or unsubstituted alkyl or substituted or unsubstituted aryl.

28. A monodentate chiral phosphine ligand, according to claim 26, selected from the compounds of the following formulas and the corresponding enantiomers:

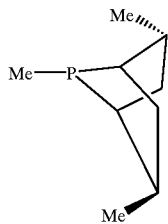

-continued

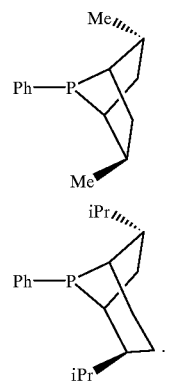

29. A monodentate chiral phosphine ligand according to claim 28, selected from a compound of the following formula and the corresponding enantiomer:

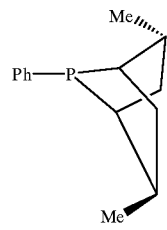

* * * * *

UNITED STATES PATENT AND TRADEMARK OFFICE
CERTIFICATE OF CORRECTION

| | | |
|---|---|---|
| PATENT NO. | : 6,037,500 | Page 1 of 1 |
| APPLICATION NO. | : 08/876120 | |
| DATED | : March 14, 2000 | |
| INVENTOR(S) | : Xumu Zhang | |

It is certified that error appears in the above-identified patent and that said Letters Patent is hereby corrected as shown below:

Column 1, Line 10, after priority claim and before "TECHNICAL FIELD OF THE INVENTION" insert the following:

-- GOVERNMENT SPONSORSHIP

This invention was made with Government support under Contract No. N00014-96-1-0733, awarded by the Office of Naval Research. The Government has certain rights in the invention. --

Signed and Sealed this

Nineteenth Day of August, 2008

JON W. DUDAS
*Director of the United States Patent and Trademark Office*